US008109966B2

(12) United States Patent
Ritchart et al.

(10) Patent No.: US 8,109,966 B2
(45) Date of Patent: *Feb. 7, 2012

(54) METHODS FOR ATTACHING CONNECTIVE TISSUES TO BONE USING A MULTI-COMPONENT ANCHOR

(75) Inventors: Mark A. Ritchart, Murrieta, CA (US); Seth A. Foerster, San Clemente, CA (US)

(73) Assignee: ArthroCare Corporation, Austin, TX (US)

( * ) Notice: Subject to any disclaimer, the term of this patent is extended or adjusted under 35 U.S.C. 154(b) by 442 days.

This patent is subject to a terminal disclaimer.

(21) Appl. No.: 11/779,194

(22) Filed: Jul. 17, 2007

(65) Prior Publication Data
US 2008/0015594 A1 Jan. 17, 2008

Related U.S. Application Data

(60) Continuation of application No. 10/327,546, filed on Dec. 20, 2002, now Pat. No. 7,247,164, which is a division of application No. 09/475,495, filed on Dec. 30, 1999, now Pat. No. 6,524,317.

(51) Int. Cl.
*A61B 17/04* (2006.01)

(52) U.S. Cl. ......... 606/232; 606/300; 606/323; 606/327

(58) Field of Classification Search .................. 128/898; 606/232, 221, 69, 70, 71, 72, 73, 148, 60, 606/61, 78, 105, 300, 323; 623/14.12, 14.13, 623/14, 623/14.14
See application file for complete search history.

(56) References Cited

U.S. PATENT DOCUMENTS

| 918,570 | A | 4/1909 | Mather ........................ 292/318 |
| 1,153,053 | A | 9/1915 | Forster ......................... 43/44.85 |
| 1,565,041 | A | 12/1925 | Arneu ......................... 24/129 R |
| 2,269,963 | A | 1/1942 | Wrapler ........................ 604/604 |
| 2,485,531 | A | 10/1949 | Dzus et al. ...................... 128/92 |
| 2,600,395 | A | 6/1952 | Domoj et al. ..................... 87/13 |
| 3,143,916 | A | 8/1964 | Rice ................................ 85/71 |
| 3,942,407 | A | 3/1976 | Mortensen ....................... 85/71 |
| 3,946,740 | A | 3/1976 | Bassett .......................... 128/334 |

(Continued)

FOREIGN PATENT DOCUMENTS
DE   3509417   9/1986
(Continued)

OTHER PUBLICATIONS

PCT Search Report and Written Opinion for PCT/US06/20657 7pgs, Mailed Oct. 2, 2007.

(Continued)

*Primary Examiner* — Tuan Nguyen
(74) *Attorney, Agent, or Firm* — Matthew Scheele; Brian Szymczak

(57) ABSTRACT

An innovative bone anchor and methods for securing connective tissue, such as tendons, to bone are disclosed which permit a suture attachment which lies entirely beneath the cortical bone surface, and wherein the suturing material between the connective tissue and the bone anchor is oriented in a direction generally transverse to the longitudinal axis of the bone anchor, so that axial pull-out forces exerted on the bone anchor are minimized. The suture attachment to the bone anchor involves the looping of a substantial length of suturing material around a shaft of the anchor, thereby avoiding an eyelet connection which requires a knot and which concentrates stress on a very small portion of the suturing material. Thus, failure rates are greatly decreased over conventional techniques, and the inventive procedures are significantly easier to perform than conventional techniques.

17 Claims, 19 Drawing Sheets

U.S. PATENT DOCUMENTS

| | | | |
|---|---|---|---|
| 3,994,521 A | 11/1976 | Van Gompel | 292/319 |
| 4,109,658 A | 8/1978 | Hughes | 128/340 |
| 4,210,148 A | 7/1980 | Stivala | 606/232 |
| 4,274,324 A | 6/1981 | Giannuzzi | 411/38 |
| 4,301,551 A | 11/1981 | Dore et al. | 623/13.3 |
| 4,319,428 A | 3/1982 | Fox | 47/42 |
| 4,345,601 A | 8/1982 | Fukuda | 128/339 |
| 4,373,530 A | 2/1983 | Kilejian | 128/334 R |
| 4,384,389 A | 5/1983 | Sato | 24/136 K |
| 4,409,974 A | 10/1983 | Freedland | 128/92 |
| 4,467,478 A | 8/1984 | Jurgutis | 606/75 |
| 4,483,023 A | 11/1984 | Hoffman, Jr. et al. | 623/13.15 |
| 4,493,323 A | 1/1985 | Albright et al. | 128/340 |
| 4,580,936 A | 4/1986 | Francis et al. | 411/38 |
| 4,590,928 A | 5/1986 | Hunt et al. | 606/72 |
| 4,597,776 A | 7/1986 | Ullman et al. | 48/197 R |
| 4,605,414 A | 8/1986 | Czajka | 623/13.11 |
| 4,621,640 A | 11/1986 | Mulhollan et al. | 128/340 |
| 4,635,637 A | 1/1987 | Schreiber | 128/337 |
| 4,657,461 A | 4/1987 | Smith | 411/340 |
| 4,672,957 A | 6/1987 | Hourahane | 606/80 |
| 4,680,835 A | 7/1987 | Horng | 24/712.5 |
| 4,712,542 A | 12/1987 | Daniel et al. | 606/96 |
| 4,721,103 A | 1/1988 | Freedland | 128/92 |
| 4,731,084 A | 3/1988 | Dunn et al. | 623/13.19 |
| 4,738,255 A | 4/1988 | Goble et al. | 128/92 YF |
| 4,741,330 A | 5/1988 | Hayhurst | 123/43 R |
| 4,750,492 A | 6/1988 | Jacobs | 606/230 |
| 4,772,286 A | 9/1988 | Goble et al. | 623/13.14 |
| 4,779,616 A | 10/1988 | Johnson et al. | 606/148 |
| 4,809,695 A | 3/1989 | Abrahamson | 24/136 K |
| 4,823,780 A | 4/1989 | Odensten et al. | 606/96 |
| 4,828,439 A | 5/1989 | Giannuzzi | 411/37 |
| 4,851,005 A | 7/1989 | Hunt et al. | 623/18 |
| 4,870,957 A | 10/1989 | Goble et al. | 606/73 |
| 4,917,700 A | 4/1990 | Aikins | 623/13.19 |
| 4,926,860 A | 5/1990 | Stice et al. | 606/144 |
| 4,935,027 A | 6/1990 | Yoon | 606/146 |
| 4,946,467 A | 8/1990 | Ohi et al. | 606/228 |
| 4,946,468 A | 8/1990 | Li | 606/232 |
| 4,957,498 A | 9/1990 | Caspari | 606/146 |
| 4,968,315 A | 11/1990 | Gatturna | 606/72 |
| 4,981,149 A | 1/1991 | Yoon et al. | 128/898 |
| 4,987,665 A | 1/1991 | Dumican | 28/218 |
| 5,002,550 A | 3/1991 | Li | 606/139 |
| 5,019,093 A | 5/1991 | Kaplan et al. | 606/228 |
| 5,037,422 A | 8/1991 | Hayhurst | 606/72 |
| 5,046,513 A | 9/1991 | Gatturna | 128/898 |
| 5,059,201 A | 10/1991 | Asnis | 606/144 |
| 5,062,344 A | 11/1991 | Gerker | 87/8 |
| 5,085,661 A | 2/1992 | Moss | 606/139 |
| 5,147,166 A | 9/1992 | Harker | 411/29 |
| 5,195,542 A | 3/1993 | Gazielly et al. | 60/244 |
| 5,203,787 A | 4/1993 | Noblitt et al. | 606/232 |
| 5,217,495 A | 6/1993 | Kaplan et al. | 623/13.18 |
| 5,219,359 A | 6/1993 | McQuilkin et al. | 606/232 |
| 5,224,946 A | 7/1993 | Hayhurst | 606/72 |
| 5,258,016 A | 11/1993 | DiPoto et al. | 606/232 |
| 5,263,984 A | 11/1993 | Li | 623/13.18 |
| 5,275,176 A | 1/1994 | Chandler | 606/242 |
| 5,304,184 A | 4/1994 | Hathaway et al. | 606/144 |
| 5,306,290 A | 4/1994 | Martins et al. | 606/232 |
| 5,324,308 A | 6/1994 | Pierce | 606/232 |
| 5,326,205 A | 7/1994 | Anspach, III et al. | 411/43 |
| 5,330,442 A | 7/1994 | Green | 606/232 |
| 5,330,468 A | 7/1994 | Burkhart | 606/96 |
| 5,330,488 A | 7/1994 | Goldrath | 606/148 |
| 5,336,240 A | 8/1994 | Metzler | 606/232 |
| 5,354,298 A | 10/1994 | Lee et al. | 606/72 |
| 5,364,407 A | 11/1994 | Poll | 606/139 |
| 5,376,118 A | 12/1994 | Kaplan et al. | 623/23.72 |
| 5,383,905 A | 1/1995 | Gold et al. | 606/232 |
| 5,405,352 A | 4/1995 | Weston | 606/148 |
| 5,405,359 A | 4/1995 | Pierce | 606/232 |
| 5,411,523 A | 5/1995 | Goble | 606/232 |
| 5,413,579 A | 5/1995 | Tom Du | 606/87 |
| 5,417,691 A | 5/1995 | Hayhurst | 606/72 |
| 5,417,699 A | 5/1995 | Klein et al. | 606/139 |
| 5,417,712 A | 5/1995 | Whitaker et al. | 606/232 |
| 5,431,666 A | 7/1995 | Sauer et al. | 606/139 |
| 5,441,508 A | 8/1995 | Gazielly et al. | 606/151 |
| 5,445,167 A | 8/1995 | Yoon et al. | 128/898 |
| 5,450,860 A | 9/1995 | O'Connor | 606/224 |
| 5,454,823 A | 10/1995 | Richardson et al. | 606/148 |
| 5,464,427 A | 11/1995 | Curtis et al. | 606/232 |
| 5,470,335 A | 11/1995 | Du Toit | 606/73 |
| 5,472,452 A | 12/1995 | Trott | 606/232 |
| 5,480,403 A | 1/1996 | Lee et al. | 606/72 |
| 5,486,197 A | 1/1996 | Le et al. | 606/232 |
| 5,499,991 A | 3/1996 | Garman et al. | 606/148 |
| 5,501,683 A | 3/1996 | Trott | 606/72 |
| 5,501,695 A | 3/1996 | Anspach, Jr. et al. | 606/72 |
| 5,505,735 A | 4/1996 | Li | 606/72 |
| 5,514,159 A | 5/1996 | Matula et al. | 606/232 |
| 5,520,700 A | 5/1996 | Beyar et al. | 606/139 |
| 5,522,820 A | 6/1996 | Caspari et al. | 606/148 |
| 5,527,322 A | 6/1996 | Klein et al. | 606/144 |
| 5,527,343 A | 6/1996 | Bonutti | 606/232 |
| 5,531,763 A | 7/1996 | Mastri et al. | 606/148 |
| 5,531,792 A | 7/1996 | Huene | 623/16 |
| 5,534,012 A | 7/1996 | Bonutti | 606/232 |
| 5,540,703 A | 7/1996 | Barker, Jr. et al. | 606/139 |
| 5,545,180 A | 8/1996 | Le et al. | 606/232 |
| 5,549,617 A | 8/1996 | Green et al. | 606/144 |
| 5,549,630 A | 8/1996 | Bonutti | 606/232 |
| 5,553,360 A | 9/1996 | Lucas et al. | 24/136 K |
| 5,562,689 A | 10/1996 | Green et al. | 606/151 |
| 5,569,305 A | 10/1996 | Bonutti | 606/232 |
| 5,569,306 A | 10/1996 | Thal | 606/232 |
| 5,571,104 A | 11/1996 | Li | 606/72 |
| 5,571,120 A | 11/1996 | Yoon | 606/148 |
| 5,573,540 A | 11/1996 | Yoon | 606/139 |
| 5,573,542 A | 11/1996 | Stevens | 606/144 |
| 5,573,548 A | 11/1996 | Nazre et al. | 606/232 |
| 5,575,801 A | 11/1996 | Habermeyer et al. | 606/148 |
| 5,584,835 A | 12/1996 | Greenfield | 606/73 |
| 5,584,839 A | 12/1996 | Gieringer | 606/96 |
| 5,584,860 A | 12/1996 | Goble et al. | 606/232 |
| 5,584,862 A | 12/1996 | Bonutti | 606/232 |
| 5,591,207 A | 1/1997 | Coleman | 606/232 |
| 5,593,189 A | 1/1997 | Little | 289/17 |
| 5,601,558 A | 2/1997 | Torrie et al. | 606/72 |
| 5,609,597 A | 3/1997 | Lehrer | 606/139 |
| 5,613,974 A | 3/1997 | Andreas et al. | 606/144 |
| 5,618,290 A | 4/1997 | Toy et al. | 606/139 |
| 5,618,314 A | 4/1997 | Harwin et al. | 606/232 |
| 5,626,614 A | 5/1997 | Hart | 606/232 |
| 5,630,824 A | 5/1997 | Hart | 606/139 |
| 5,632,748 A | 5/1997 | Beck, Jr. et al. | 606/72 |
| 5,645,589 A | 7/1997 | Li | 623/16 |
| 5,647,874 A | 7/1997 | Hayhurst | 606/72 |
| 5,649,940 A | 7/1997 | Hart et al. | 606/148 |
| 5,658,313 A | 8/1997 | Thal | 606/232 |
| 5,665,110 A | 9/1997 | Chervitz et al. | 606/232 |
| 5,665,112 A | 9/1997 | Thal | 606/232 |
| 5,667,528 A | 9/1997 | Colligan | 606/224 |
| D385,352 S | 10/1997 | Bales et al. | |
| 5,681,333 A | 10/1997 | Burkhart et al. | 606/148 |
| 5,681,351 A | 10/1997 | Jamiolkowski | 606/232 |
| 5,683,418 A | 11/1997 | Luscombe et al. | 606/232 |
| 5,683,419 A | 11/1997 | Thai | 606/232 |
| 5,690,649 A | 11/1997 | Li | 606/139 |
| 5,693,060 A | 12/1997 | Martin | 606/148 |
| 5,697,950 A | 12/1997 | Fucci et al. | 606/232 |
| 5,702,397 A | 12/1997 | Goble et al. | 606/72 |
| 5,702,398 A | 12/1997 | Tarabishy | |
| 5,707,362 A | 1/1998 | Yoon | 604/164 |
| 5,707,394 A | 1/1998 | Miller et al. | 606/232 |
| 5,709,708 A | 1/1998 | Thal | 606/232 |
| 5,720,765 A | 2/1998 | Thal | 606/232 |
| 5,725,529 A | 3/1998 | Nicholson et al. | 606/72 |
| 5,725,541 A | 3/1998 | Anspach, III et al. | 606/151 |
| 5,728,136 A | 3/1998 | Thal | 606/232 |
| 5,733,307 A | 3/1998 | Dinsdale | 606/232 |
| 5,741,281 A | 4/1998 | Martin | 606/148 |
| 5,741,282 A | 4/1998 | Anspach, III et al. | 606/151 |
| 5,766,250 A | 6/1998 | Chervitz et al. | 623/13 |

| Patent No. | Date | Inventor | Class |
|---|---|---|---|
| 5,782,863 A | 7/1998 | Bartlett | 606/232 |
| 5,782,864 A | 7/1998 | Lizardi | 606/232 |
| 5,782,865 A | 7/1998 | Grotz | 606/72 |
| 5,791,899 A | 8/1998 | Sachdeva | 433/173 |
| 5,792,152 A | 8/1998 | Klein et al. | 606/144 |
| 5,797,927 A | 8/1998 | Yoon | 606/144 |
| 5,797,963 A | 8/1998 | McDevitt | 606/232 |
| 5,810,848 A | 9/1998 | Hayhurst | 606/144 |
| 5,810,854 A | 9/1998 | Beach | 606/232 |
| 5,814,052 A | 9/1998 | Nakao et al. | 606/148 |
| 5,814,071 A | 9/1998 | McDevitt et al. | 606/232 |
| 5,814,072 A | 9/1998 | Bonutti | 606/232 |
| 5,843,111 A | 12/1998 | Vijfvinkel | 606/171 |
| 5,849,004 A | 12/1998 | Bramlet | 606/232 |
| 5,860,978 A | 1/1999 | McDevitt | 606/72 |
| 5,860,991 A | 1/1999 | Klein et al. | 606/144 |
| 5,860,992 A | 1/1999 | Daniel et al. | 606/145 |
| 5,868,789 A | 2/1999 | Heubner | 606/232 |
| 5,879,372 A | 3/1999 | Bartlett | 606/232 |
| 5,882,340 A | 3/1999 | Yoon | 604/164 |
| 5,885,294 A | 3/1999 | Pedlick et al. | 606/80 |
| 5,891,168 A | 4/1999 | Thal | 606/232 |
| 5,893,850 A | 4/1999 | Cachia | 606/72 |
| 5,902,311 A | 5/1999 | Andreas et al. | 606/144 |
| 5,904,692 A | 5/1999 | Steckel et al. | 606/139 |
| 5,911,721 A | 6/1999 | Nicholson et al. | 606/72 |
| 5,921,994 A | 7/1999 | Andreas et al. | 606/144 |
| 5,935,107 A | 8/1999 | Taylor et al. | 604/164 |
| 5,935,129 A | 8/1999 | Mdevitt et al. | 606/72 |
| 5,941,900 A | 8/1999 | Bonutti | 606/232 |
| 5,941,901 A | 8/1999 | Egan | 606/232 |
| 5,944,724 A | 8/1999 | Lizardi | 606/104 |
| 5,944,739 A | 8/1999 | Zlock et al. | 606/232 |
| 5,947,982 A | 9/1999 | Duran | 606/139 |
| 5,948,000 A | 9/1999 | Larsen et al. | 606/232 |
| 5,948,001 A | 9/1999 | Larsen | 606/232 |
| 5,948,002 A | 9/1999 | Bonutti | 606/232 |
| 5,957,953 A * | 9/1999 | DiPoto et al. | 606/232 |
| 5,957,968 A | 9/1999 | Belden et al. | 607/126 |
| 5,961,530 A | 10/1999 | Moore et al. | 606/148 |
| 5,961,538 A | 10/1999 | Pedlick et al. | 606/232 |
| 5,968,044 A | 10/1999 | Nicholson et al. | 606/72 |
| 5,980,558 A | 11/1999 | Wiley | 606/232 |
| 5,980,559 A | 11/1999 | Bonutti | 606/232 |
| 5,984,933 A | 11/1999 | Yoon | 606/148 |
| 5,993,459 A | 11/1999 | Larsen | 606/104 |
| 6,001,104 A | 12/1999 | Benderev et al. | 606/80 |
| 6,001,109 A | 12/1999 | Kontos | 606/148 |
| 6,007,566 A | 12/1999 | Wenstrom | 606/232 |
| 6,007,567 A | 12/1999 | Bonutti | 606/232 |
| 6,010,525 A | 1/2000 | Bonutti et al. | 606/232 |
| 6,013,083 A | 1/2000 | Bennett | 606/104 |
| 6,017,346 A | 1/2000 | Grotz | 606/72 |
| 6,022,360 A | 2/2000 | Reimels et al. | 606/144 |
| 6,022,373 A | 2/2000 | Li | 606/232 |
| 6,024,758 A | 2/2000 | Thal | 606/232 |
| 6,033,430 A | 3/2000 | Bonutti | 606/232 |
| 6,036,699 A | 3/2000 | Andreas et al. | 606/139 |
| 6,045,571 A | 4/2000 | Hill et al. | 606/228 |
| 6,045,572 A | 4/2000 | Johnson et al. | 606/232 |
| 6,045,573 A | 4/2000 | Wenstrom et al. | 606/232 |
| 6,045,574 A | 4/2000 | Thal | 606/232 |
| 6,048,351 A | 4/2000 | Gordon et al. | 606/144 |
| 6,051,006 A | 4/2000 | Shluzas et al. | 606/148 |
| 6,053,935 A | 4/2000 | Brenneman et al. | 606/232 |
| 6,056,773 A | 5/2000 | Bonutti | 606/232 |
| 6,066,146 A | 5/2000 | Carroll et al. | 606/148 |
| 6,068,648 A | 5/2000 | Cole et al. | 606/232 |
| 6,086,608 A | 7/2000 | Elk et al. | 606/232 |
| 6,096,051 A | 8/2000 | Kortenbach et al. | 606/144 |
| 6,102,934 A | 8/2000 | Li | 606/232 |
| 6,117,160 A | 9/2000 | Bonutti | 606/215 |
| 6,117,161 A | 9/2000 | Li | 606/232 |
| 6,143,004 A | 11/2000 | Davis et al. | 606/144 |
| 6,146,386 A | 11/2000 | Blackman | 606/103 |
| 6,146,406 A | 11/2000 | Shluzas et al. | 606/232 |
| 6,149,669 A | 11/2000 | Li | 606/232 |
| 6,156,039 A | 12/2000 | Thal | 606/72 |
| 6,156,056 A | 12/2000 | Kearns et al. | 606/232 |
| 6,159,235 A | 12/2000 | Kim | 606/232 |
| 6,162,537 A | 12/2000 | Martin et al. | 428/373 |
| 6,171,317 B1 | 1/2001 | Jackson et al. | 606/148 |
| 6,200,329 B1 | 3/2001 | Fung et al. | 606/232 |
| 6,200,893 B1 | 3/2001 | Sneh | 438/685 |
| 6,206,895 B1 | 3/2001 | Levison | 606/144 |
| 6,217,592 B1 | 4/2001 | Freda et al. | 606/145 |
| 6,221,107 B1 | 4/2001 | Steiner et al. | 623/13.14 |
| 6,228,096 B1 | 5/2001 | Marchand | 606/139 |
| 6,241,736 B1 | 6/2001 | Sater | 606/104 |
| 6,267,766 B1 | 7/2001 | Burkhart | 606/72 |
| 6,280,474 B1 | 8/2001 | Cassidy et al. | 623/16.11 |
| 6,293,961 B2 | 9/2001 | Schwartz | 606/232 |
| 6,315,781 B1 | 11/2001 | Reinhardt | 606/108 |
| 6,319,252 B1 | 11/2001 | McDevitt et al. | 606/60 |
| 6,319,269 B1 | 11/2001 | Li | 606/232 |
| 6,319,271 B1 | 11/2001 | Schwartz | 606/232 |
| 6,328,758 B1 | 12/2001 | Tornier et al. | 606/232 |
| 6,355,053 B1 | 3/2002 | Li | 606/232 |
| 6,409,743 B1 | 6/2002 | Fenton | 606/232 |
| 6,432,123 B2 | 8/2002 | Schwartz et al. | 606/232 |
| 6,436,109 B1 | 8/2002 | Kontes | 606/148 |
| 6,451,030 B2 | 9/2002 | Li et al. | 606/139 |
| 6,464,713 B2 | 10/2002 | Bonutti | 606/232 |
| 6,468,293 B2 | 10/2002 | Bonutti et al. | 606/232 |
| 6,471,715 B1 | 10/2002 | Weiss | 606/216 |
| 6,475,230 B1 | 11/2002 | Bonutti et al. | 606/232 |
| 6,491,714 B1 | 12/2002 | Bennett | 606/232 |
| 6,517,542 B1 | 2/2003 | Papay et al. | 606/73 |
| 6,520,980 B1 | 2/2003 | Foerster | 606/232 |
| 6,524,317 B1 | 2/2003 | Ritchart et al. | 606/72 |
| 6,527,794 B1 | 3/2003 | McDevitt et al. | 606/232 |
| 6,540,770 B1 | 4/2003 | Tornier et al. | 606/232 |
| 6,569,187 B1 | 5/2003 | Bonutti et al. | 606/232 |
| 6,575,987 B2 | 6/2003 | Appell et al. | 606/151 |
| 6,582,453 B1 | 6/2003 | Tran et al. | 606/232 |
| 6,585,730 B1 | 7/2003 | Foerster | 606/232 |
| 6,635,073 B2 | 10/2003 | Bonutti | 606/232 |
| 6,638,279 B2 | 10/2003 | Bonutti | 606/60 |
| 6,645,227 B2 | 11/2003 | Fallin et al. | 606/232 |
| 6,648,903 B1 | 11/2003 | Pierson, III | 606/232 |
| 6,652,561 B1 | 11/2003 | Tran | 606/232 |
| 6,656,183 B2 | 12/2003 | Colleran et al. | 606/232 |
| 6,660,008 B1 | 12/2003 | Foerster et al. | 606/72 |
| 6,660,023 B2 | 12/2003 | McDevitt et al. | 606/232 |
| 6,679,896 B2 | 1/2004 | Gellman et al. | 606/148 |
| 6,682,549 B2 | 1/2004 | Bartlett | 606/232 |
| 6,689,154 B2 | 2/2004 | Bartlett | 606/232 |
| 6,692,516 B2 | 2/2004 | West et al. | 606/232 |
| 6,736,829 B1 | 5/2004 | Li et al. | 606/232 |
| 6,770,076 B2 | 8/2004 | Foerster | 606/72 |
| 6,780,198 B1 | 8/2004 | Gregoire et al. | 606/232 |
| 6,855,157 B2 | 2/2005 | Foerster et al. | 606/232 |
| 6,860,887 B1 | 3/2005 | Frankie | 606/104 |
| 6,939,379 B2 | 9/2005 | Sklar | 623/13.14 |
| 6,972,027 B2 | 12/2005 | Fallin et al. | 606/232 |
| 7,083,638 B2 | 8/2006 | Foerster | 606/232 |
| 7,087,064 B1 | 8/2006 | Hyde | 606/142 |
| 7,090,690 B2 | 8/2006 | Foerster et al. | 606/232 |
| 7,104,999 B2 | 9/2006 | Overaker | 606/142 |
| 7,150,750 B2 | 12/2006 | Damarati | 623/17.11 |
| 7,150,757 B2 | 12/2006 | Fallin et al. | 606/232 |
| 7,247,164 B1 | 7/2007 | Ritchart et al. | 606/232 |
| 7,329,272 B2 | 2/2008 | Burkhart et al. | 606/232 |
| 7,556,640 B2 | 7/2009 | Foerster | 606/232 |
| 7,588,587 B2 | 9/2009 | Barbieri et al. | 606/232 |
| 7,615,061 B2 | 11/2009 | White et al. | 606/148 |
| 7,637,926 B2 | 12/2009 | Foerster et al. | 606/232 |
| 7,674,274 B2 | 3/2010 | Foerster et al. | 606/232 |
| 7,682,374 B2 | 3/2010 | Foerster | 606/72 |
| 7,695,494 B2 | 4/2010 | Foerster | 606/232 |
| 2003/0167062 A1 | 9/2003 | Gambale | 606/232 |
| 2003/0191498 A1 | 10/2003 | Foerster et al. | 606/232 |
| 2003/0195563 A1 | 10/2003 | Foerster | 606/232 |
| 2003/0195564 A1 | 10/2003 | Tran et al. | 606/232 |
| 2004/0138706 A1 | 7/2004 | Abrams et al. | 606/232 |
| 2004/0236336 A1 | 11/2004 | Foerster et al. | 606/72 |
| 2004/0260345 A1 | 12/2004 | Foerster | 606/232 |
| 2005/0033364 A1 | 2/2005 | Gregoire et al. | 606/232 |

| | | | |
|---|---|---|---|
| 2005/0080455 A1 | 4/2005 | Schmieding et al. | 606/232 |
| 2005/0090827 A1 | 4/2005 | Gedebou | 606/72 |
| 2005/0240226 A1 | 10/2005 | Foerster et al. | 606/232 |
| 2005/0277986 A1 | 12/2005 | Foerster | 606/232 |
| 2006/0004364 A1 | 1/2006 | Green et al. | 606/72 |
| 2006/0074422 A1 | 4/2006 | Story et al. | 606/142 |
| 2006/0079904 A1 | 4/2006 | Thal | 606/72 |
| 2006/0161159 A1 | 7/2006 | Dreyfuss et al. | 606/72 |
| 2006/0271060 A1 | 11/2006 | Gordon | 606/232 |
| 2006/0271105 A1 | 11/2006 | Foerster | 606/232 |
| 2006/0293710 A1 | 12/2006 | Foerster | 606/72 |
| 2007/0142838 A1 | 6/2007 | Jordan | 606/75 |
| 2007/0203508 A1 | 8/2007 | White et al. | 606/148 |
| 2008/0051836 A1 | 2/2008 | Foerster et al. | 606/232 |
| 2008/0319478 A1 | 12/2008 | Foerster et al. | 606/148 |
| 2009/0069823 A1 | 3/2009 | Foerster et al. | 606/103 |
| 2009/0222040 A1 | 9/2009 | Foerster et al. | 606/232 |
| 2009/0222041 A1 | 9/2009 | Foerster et al. | 606/232 |
| 2010/0191283 A1 | 7/2010 | Foerster et al. | 606/232 |

FOREIGN PATENT DOCUMENTS

| | | |
|---|---|---|
| EP | 0 535 906 A2 | 4/1993 |
| EP | 0 571 686 A1 | 12/1993 |
| EP | 0 611 557 A2 | 8/1994 |
| EP | 1 072 234 A2 | 1/2001 |
| EP | 1 072 237 A1 | 1/2001 |
| FR | 2777442 | 10/1999 |
| FR | 2777447 | 10/1999 |
| JP | 2286468 | 11/1990 |
| JP | 8-52154 | 2/1996 |
| JP | 08-206121 | 8/1996 |
| JP | 11-502437 | 3/1999 |
| JP | 2000-225118 | 8/2000 |
| WO | 89/10096 | 11/1989 |
| WO | 91/06247 | 5/1991 |
| WO | 95/06439 | 3/1995 |
| WO | 95/25469 | 9/1995 |
| WO | 96/28118 | 9/1996 |
| WO | 97/20522 | 6/1997 |
| WO | 99/53843 | 10/1999 |
| WO | 99/53844 | 10/1999 |
| WO | 02/21997 | 3/2002 |
| WO | 03/049620 | 6/2003 |

OTHER PUBLICATIONS

PCT Search Report and Written Opinion for PCT/US06/21125 6pgs, Mailed May 22, 2008.
PCT International Search Report for PCT/US01/21905 3pgs, Mailed Jan. 22, 2002.
PCT International Preliminary Examination Report for PCT/US01/21905 3pgs, Oct. 17, 2003.
PCT International Search Report for PCT/US01/17689 3pgs, Mailed Dec. 19, 2001.
PCT International Preliminary Examination Report for PCT/US01/17689 15pgs, Feb. 9, 2003.
PCT International Search Report for PCT/US02/17493 1pg, Mailed Mar. 27, 2003.
PCT International Preliminary Examination Report for PCT/US02/17493 4pgs, Sep. 8, 2003.
PCT International Search Report for PCT/US02/41018 2pgs, Mailed Jun. 5, 2003.
PCT International Preliminary Examination Report for PCT/US02/41018 3pgs, Feb. 22, 2004.
PCT International Search Report for PCT/US02/04231 1pg, Mailed Aug. 14, 2002.
PCT International Preliminary Examination Report for PCT/US02/04231 3pgs, Nov. 13, 2002.
PCT International Search Report for PCT/US03/35695 1pg, Mailed Feb. 14, 2005.
PCT International Preliminary Examination Report for PCT/US03/35695 4pgs, Dec. 21, 2005.
EP Partial European Search Report for EP02742470 3pgs, Apr. 13, 2004.
EP Supplementary European Search Report for EP02742470 5pgs, Jul. 30, 2004.
UK Search Report for GB 0816111.9 3pgs, Dec. 16, 2008.
European Search Report for EP 02734649 3pgs, Jan. 22, 2009.
EP Extended Search Report for EP09162639 4pgs, Oct. 28, 2009.
EP Supplementary European Search Report for EP02792506 3pgs, Mar. 24, 2010.

* cited by examiner

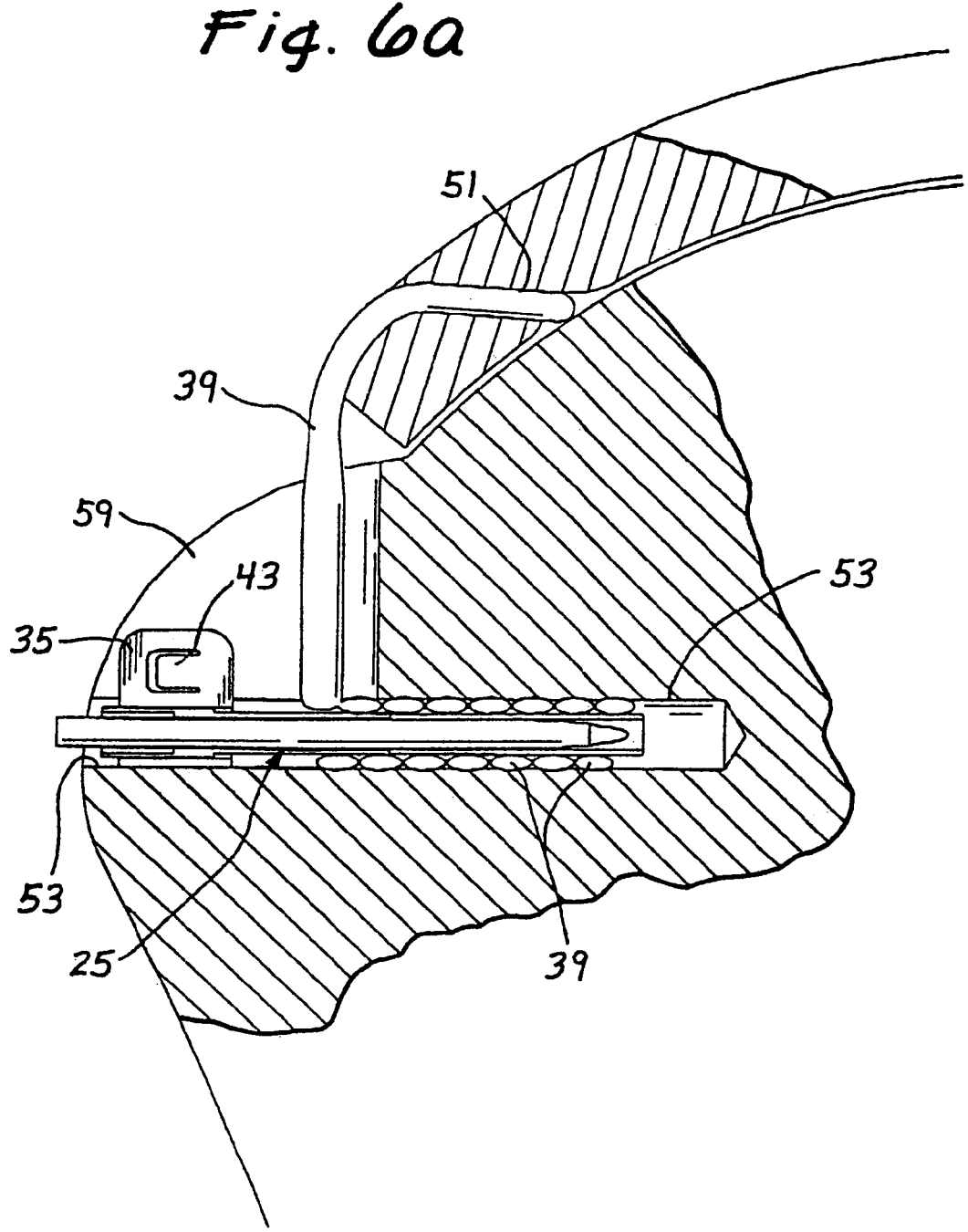

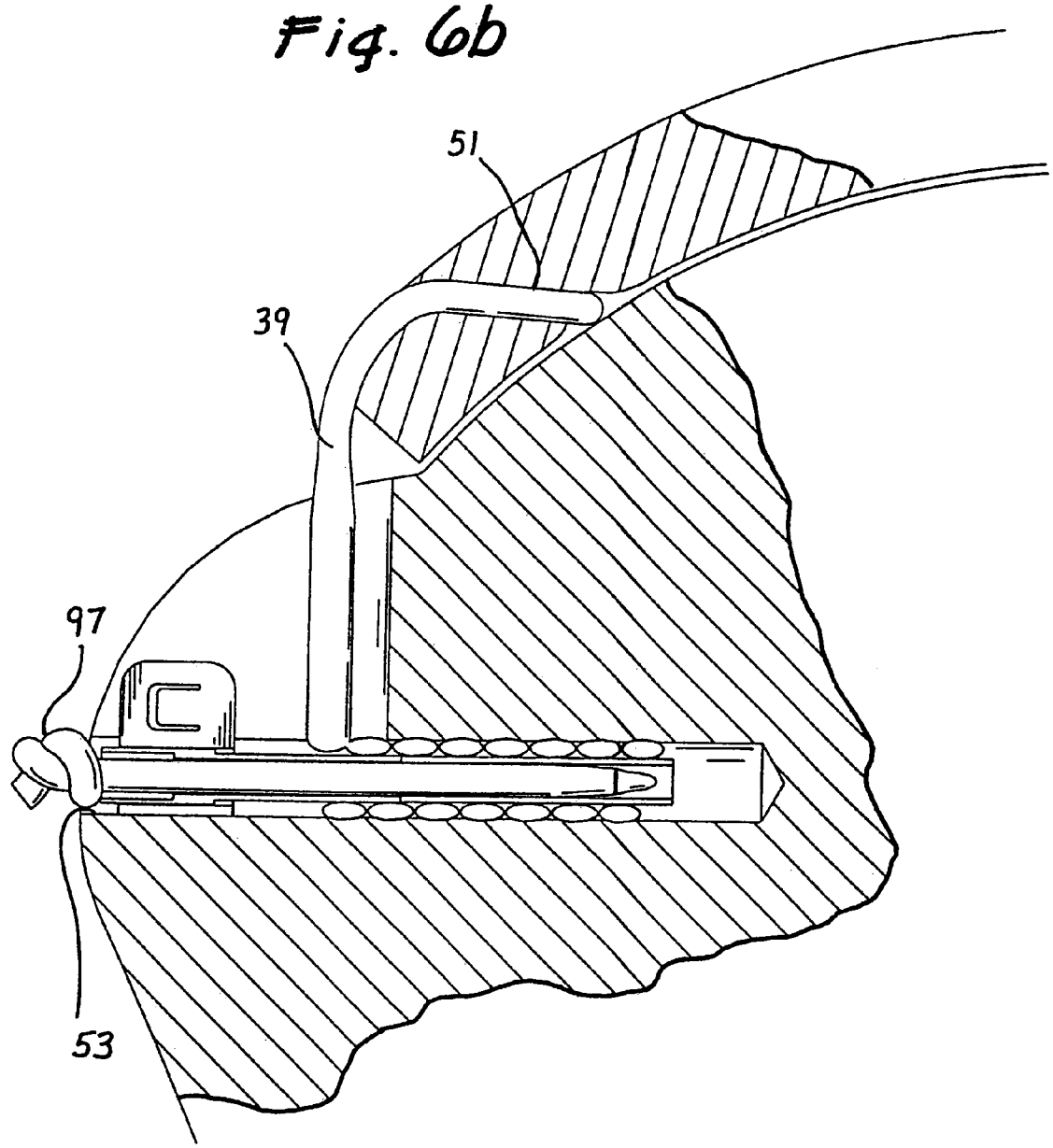

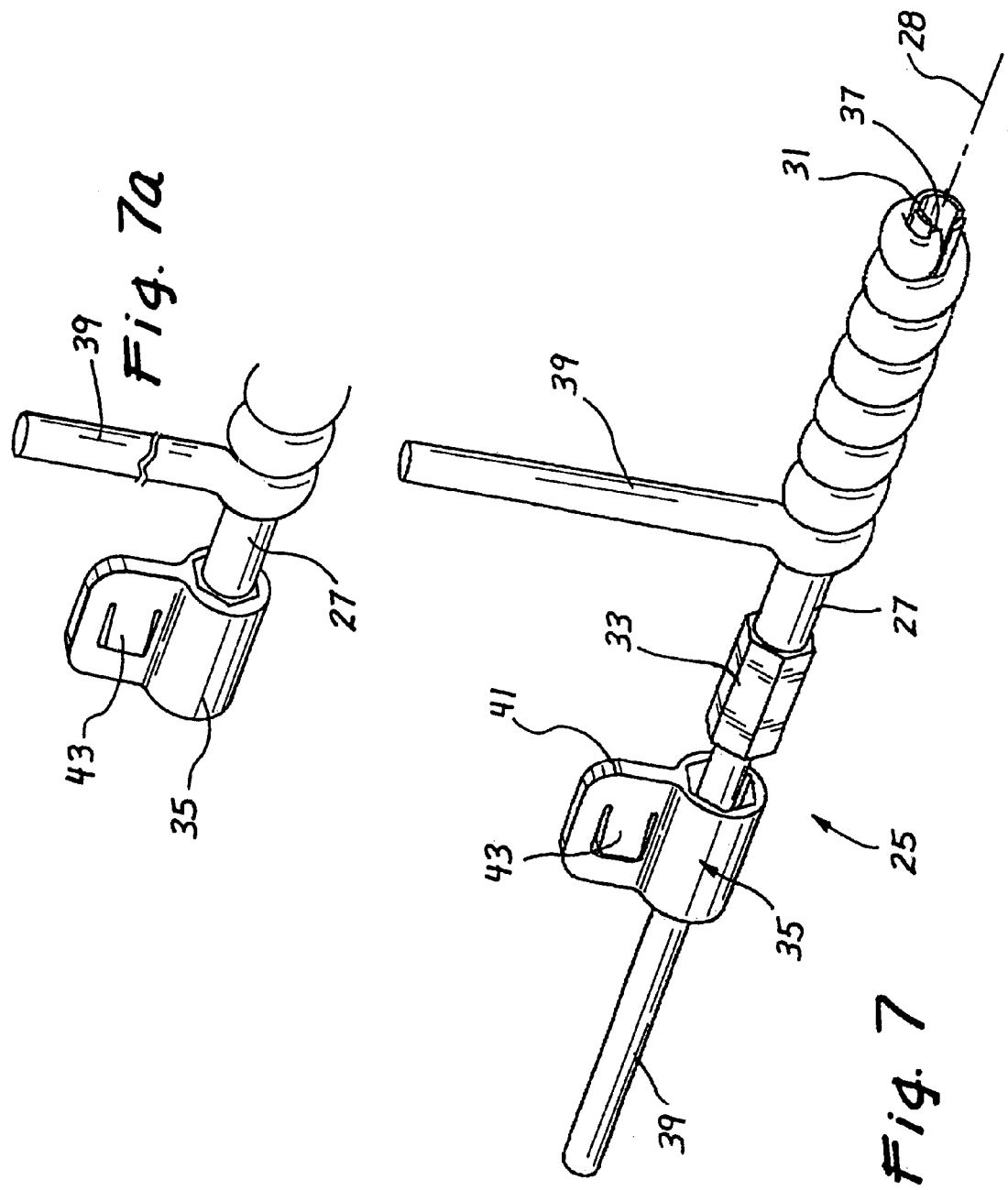

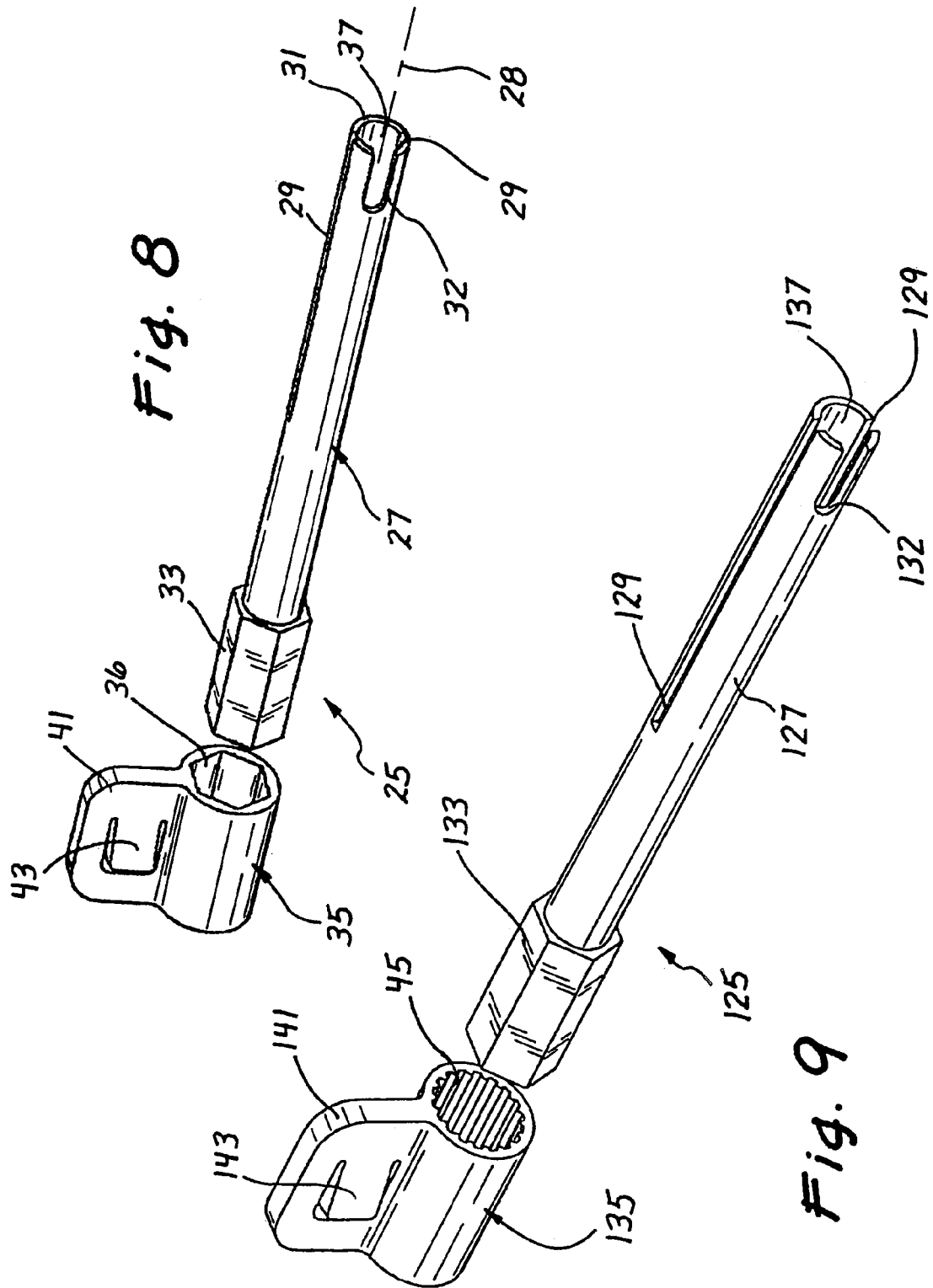

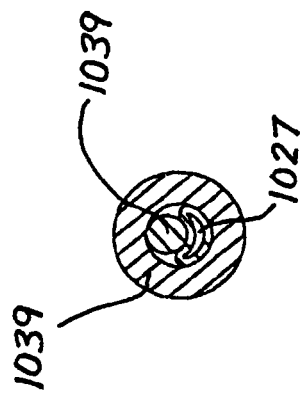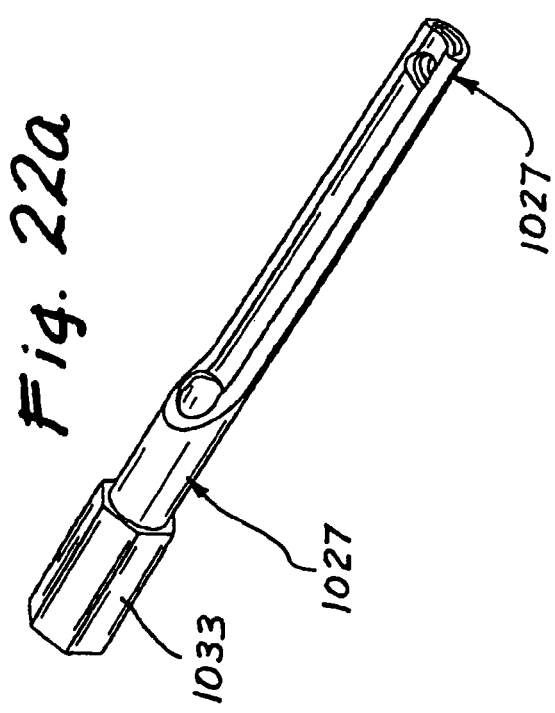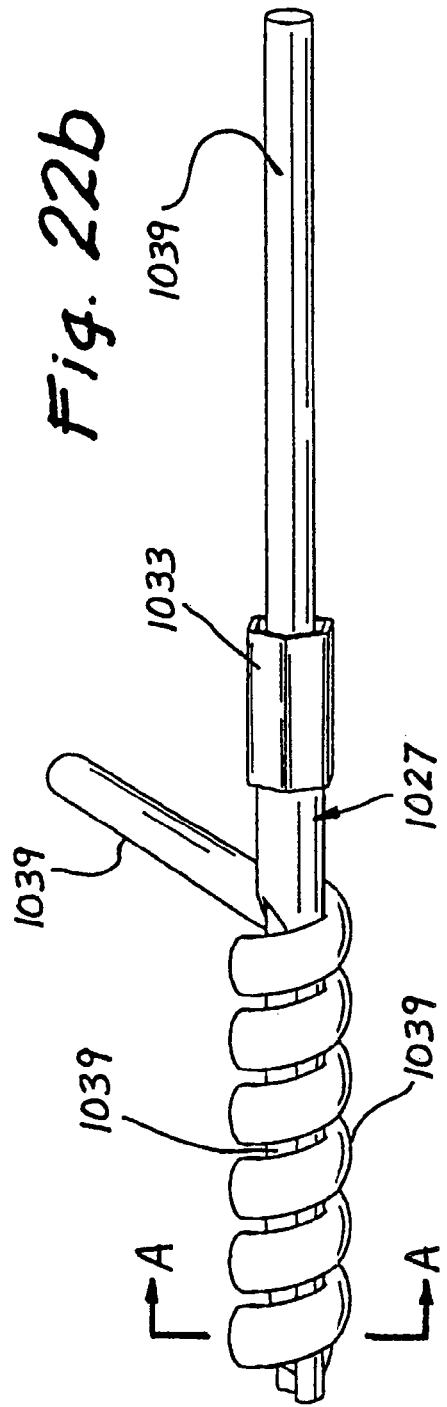

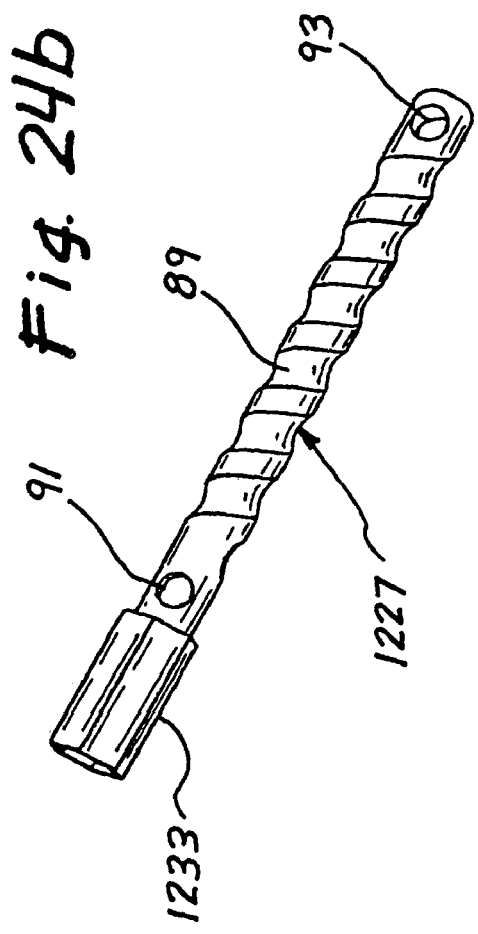
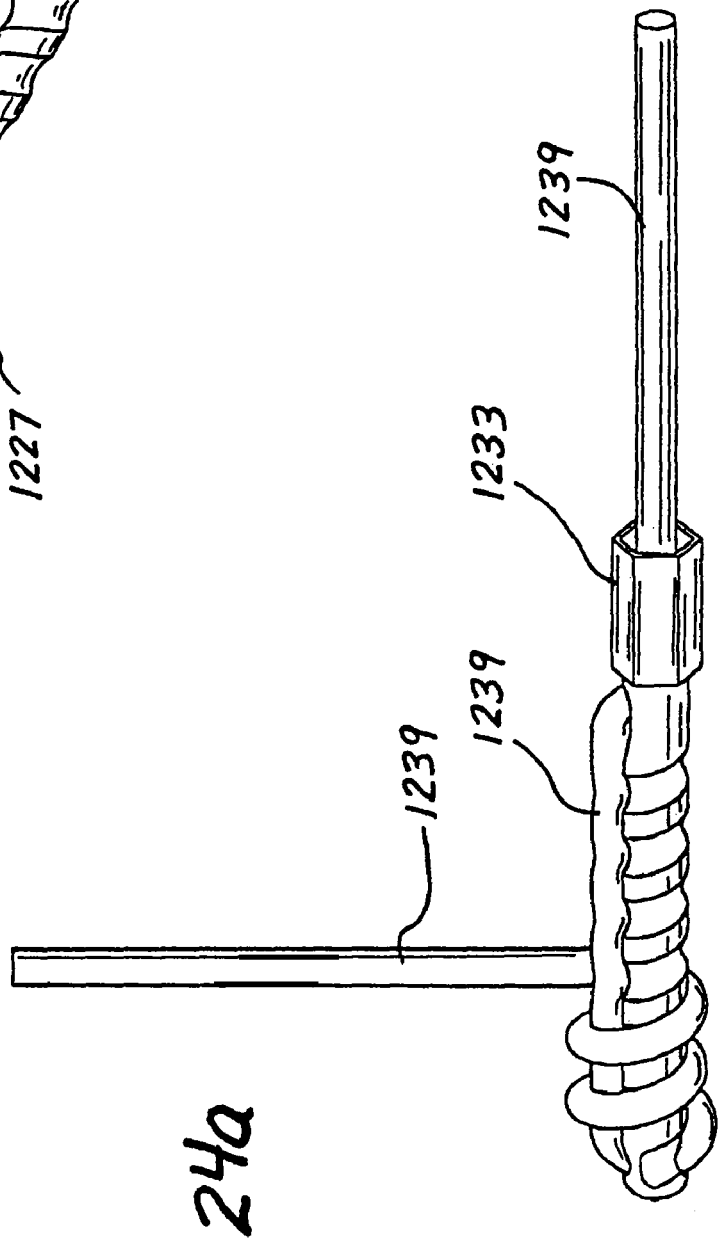

METHODS FOR ATTACHING CONNECTIVE TISSUES TO BONE USING A MULTI-COMPONENT ANCHOR

CROSS REFERENCE TO RELATED APPLICATIONS

This application is a continuation of U.S. patent application Ser. No. 10/327,546 filed Dec. 20, 2002, now U.S. Pat. No. 7,247,164, which is a divisional of U.S. patent application Ser. No. 09/475,495 filed Dec. 30, 1999, now U.S. Pat. No. 6,524,317.

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. Two types of open surgical approaches for repair of the rotator cuff, one known as the "classic open" and the other as the "mini-open". The classic open approach requires a large incision and complete detachment of the deltoid muscle from the acromion to facilitate exposure. Following the suturing of the rotator cuff to the humeral head, the detached deltoid is surgically reattached. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically used in conjunction with arthroscopic acromial decompression. Once the deltoid is split, it is retracted to expose the rotator cuff tear. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion.

Although the above described surgical technique is the current standard of care for rotator cuff repair, it is associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is less difficult, but their tightness cannot later be adjusted. Knots tied arthroscopically are difficult to achieve, impossible to adjust, and are located in less than optimal areas of the shoulder. Suture tension is also impossible to measure and adjust once the knot has been tied. Consequently, because of the technical difficulty of the procedure, presently less than 1% of all rotator cuff procedures are of the arthroscopic type, and are considered investigational in nature.

A significant difficulty with current arthroscopic rotator cuff repair techniques are shortcomings related to currently available suture anchors. Suture eyelets in bone anchors available today are small in radius, and can cause the suture to fail at that location when the anchor is placed under high tensile loads. Additionally, the sutures must be preloaded into the anchor. Thus, if the suture breaks or is accidentally pulled out during manipulation, a new anchor must be used. The old anchor remains in the bone, because of a barbed construction designed to resist axial removal of the anchor. This presents a problem because of the limited bone space available for the insertion of bone anchors. The need to utilize additional bone anchors to satisfactorily complete a procedure, leaving extra useless anchors in the bone, can severely compromise the ability to perform subsequent procedures, should they be required. Furthermore, due to design, some anchors are limited in the way that they can be placed into the bone. For example, two Mitek anchors must not be placed too near one another or too near the edge of a bone as the "retention barbs" present on anchors of this particular design would interfere with each other or fall outside the surface of the bone. A major problem with existing suture anchor designs is the location of the suture attachment point (typically an eyelet) at the exposed proximal end of the anchor. This arrangement means that any tensile force applied on the suturing material attached to the anchor will result in an axial pull-out force applied to the anchor. As a consequence, if the suturing material itself does not break at the point of attachment, as discussed supra, then there is still a substantial risk that the bone anchor will pull out of the bone, causing the connective tissue to once again become at least partially detached from the bone. In the humerus, the cancellous bone is soft, making such an event more likely. If either suture failure or anchor pull-out occurs after the surgical procedure has been completed, then an entirely new repair procedure must be initiated, with its attendant costs, discomfort, inconvenience, and rehabilitation.

Other methods of securing soft tissue to bone are known in the prior art, such as staples and tacks, but are not presently considered to be feasible for shoulder repair procedures, because of physicians' reluctance to leave anything but a suture in the capsule area of the shoulder. The reason for this is that staples, tacks, and the like could possibly fall out and cause injury during movement. Screws are also known for such attachment procedures, but suffer from a number of disadvantages, including their tendency to loosen over time, requiring a second procedure to later remove them, and their requirement for a relatively flat attachment geometry. As a result of this constraint, the attachment point often must be located at a less than ideal position.

What is needed, therefore, is a new approach for repairing the rotator cuff, wherein suture tension can be measured and adjusted, the suture resides completely below the cortical bone surface, there is no requirement for the surgeon to tie a knot to attach the suture to the bone anchor, and the skill level for correct placement is suitable for practitioners having average ability.

SUMMARY OF THE INVENTION

The present invention solves the problems outlined above by providing an innovative bone anchor and connective techniques which permit a suture attachment which lies entirely beneath the cortical bone surface, and wherein the suturing material between the connective tissue and the bone anchor is oriented in a direction generally transverse to the longitudinal axis of the bone anchor, so that axial pull-out forces exerted on the bone anchor are minimized. The suture attachment to the bone anchor involves the looping of a substantial length of suturing material around a shaft of the anchor, thereby avoiding an eyelet connection which requires a knot and which concentrates stress on a very small portion of the suturing material. Thus, failure rates are greatly decreased over conventional techniques, and the inventive procedures are significantly easier to perform than conventional techniques.

More particularly, there is provided an apparatus for attaching connective tissue to bone, comprising a shaft having a longitudinal axis and a periphery, which is adapted to be inserted into a bone. The shaft is adapted to have at least one loop of suturing material extending around the periphery thereof while the shaft is disposed in the bone. Advantageously, the shaft comprises structure, such as an anti-rotation cap, for retaining a portion of adjacent suturing material, so that subsequent rotation of the shaft causes a length of the suturing material to become wrapped about the shaft, thereby securing the suturing material to the shaft. The retaining structure preferably comprises a lumen disposed in the shaft, for channeling a length of the suturing material therealong in an axial direction.

In another aspect of the invention, there is provided an apparatus for attaching connective tissue to bone, which comprises a shaft having a longitudinal axis, which is adapted to be inserted into a bone. The apparatus also includes structure for retaining a portion of adjacent suturing material, so that subsequent rotation of the shaft causes a length of the suturing material to become wrapped about the shaft, thereby securing the suturing material to the shaft. Advantageously, an anti-rotation element, preferably comprising an anti-rotation cap or an anti-rotation bar, is disposed on the shaft, portions of which engage the bone surrounding the shaft in order to prevent the shaft from moving rotationally.

In still another aspect of the invention, an apparatus for attaching connective tissue to bone is provided which requires two or more portals in the bone to manage the tissue to bone attachment. A first one of the portals is adapted to receive suturing material which is attached at one end to the tissue to be attached to the bone. The apparatus comprises an anchoring mechanism which is adapted to be inserted into a second one of the two or more portals. The anchoring mechanism is further adapted to receiving a free end of the suturing material which extends through the first portal, and to employ rotational motion to both attach the suturing material to the anchoring mechanism and to selectively tighten the suturing material.

Importantly, the suturing material joining the tissue to the anchoring mechanism lies in a direction generally transverse to that of a longitudinal axis of the anchoring mechanism. This permits the inventive mechanism to be subjected to little or no axial "pull-out" forces, due to the attachment of the anchoring mechanism to the torn connective tissue, such as a tendon, relative to prior art suture anchors of this type, thereby sharply reducing the chance of failure of the anchoring mechanism because of its inadvertent separation from the bone.

An inventive method is disclosed for securing connective tissue to bone, which comprises a step of creating a slit in a bone, which slit is open along its length at a surface of the bone and which extends along an anticipated suture path between the connective tissue and a hole in the bone for securing an anchoring device. Other steps include attaching a first end of suturing material to the connective tissue which is to be attached to the bone, securing a second end of the suturing material to the anchoring device, and inserting the anchoring device into the hole, so that the suturing material is disposed in the slit between the anchoring device and the connective tissue. The disclosed inventive method is versatile, in that the securing step may be performed before the inserting step, the suturing material sliding downwardly into the slit through the opening on the bone surface as the anchoring device is advanced into the hole, or, alternatively, the securing step may be performed after the inserting step, if desired.

In yet another aspect of the invention, a method for securing connective tissue to bone is disclosed which comprises steps of attaching a first end of suturing material to connective tissue which is to be attached to a bone, and securing a second end of the suturing material to an anchoring device by wrapping a length thereof about the anchoring device.

In another aspect of the invention, a method for securing connective tissue to bone is disclosed which comprises steps of creating a first portal in the bone, for receiving a suture anchoring device, and creating a second portal in the bone, having an orientation generally transverse to that of the first portal, for receiving suturing material which attaches the suture anchoring device to the connective tissue. Preferably, the second portal has a slot-type geometry, while the first portal comprises a bore which is disposed generally parallel to and beneath the connective tissue, such that the second portal communicates with the first portal and with the connective tissue.

In still another aspect of the invention, there is provided an apparatus for attaching connective tissue to bone, comprising a structure having a longitudinal axis and a periphery, wherein the structure, preferably a shaft, is adapted to be inserted into a bone. At least one loop of suturing material extends around the periphery of the structure while the structure is inserted into the bone.

The invention, together with additional features and advantages thereof, may best be understood by reference to the following description taken in conjunction with the accompanying illustrative drawings.

BRIEF DESCRIPTION OF THE DRAWINGS

FIG. 6a is an enlargement of a portion of FIG. 6, illustrating in greater detail the structure and methods of the present invention;

FIG. 6b is a cross-sectional view similar to FIG. 6a, wherein a knot has been tied at the proximal end of the suturing material extending from the inventive anchoring device for retentive purposes;

FIG. 7 is a perspective view of a first preferred embodiment of a knotless suture anchoring device constructed in accordance with the principles of the invention, in a partially assembled configuration;

FIG. 7a is a perspective view similar to FIG. 7, showing the first preferred embodiment of the knotless suture anchoring device in a fully assembled configuration;

FIG. 8 is a perspective view similar to FIG. 7, illustrating the first preferred embodiment of the knotless suture anchoring device in an initial unassembled configuration;

FIG. 9 is a perspective view similar to FIG. 8, illustrating a second modified embodiment of the preferred knotless suture anchoring device;

FIG. 10b is a plan view of the embodiment illustrated in FIG. 10a;

FIG. 10c is another perspective view from another angle of the embodiment illustrated in FIG. 10a;

FIG. 11b is a perspective view from another angle of the embodiment illustrated in FIG. 11a;

FIG. 12b is a perspective view from another angle of the embodiment illustrated in FIG. 12a;

FIG. 22a is a perspective view of another modified embodiment of the inventive device, having an open shaft configuration so that suturing material which is wrapped about the shaft is in direct contact with suturing material which extends along the length of the shaft and proximally from its proximal end;

FIG. 22b is a perspective view of the embodiment shown in FIG. 22a, which shows the suturing material wrapped about the shaft;

FIG. 22c is a cross-sectional view along lines A-A of FIG. 22b;

FIG. 24a is a perspective view of still another modified embodiment of the knotless suture anchoring device of the present invention, wherein the axially extending suturing material lies on the exterior of the shaft, and peaks and valleys are provided to create a more tortuous path therefor and thus reduce slippage; and FIG. 24b is another perspective view of the device illustrated in FIG. 24a, wherein the suturing material has been removed for clarity.

DESCRIPTION OF THE PREFERRED EMBODIMENT

Figure 1:
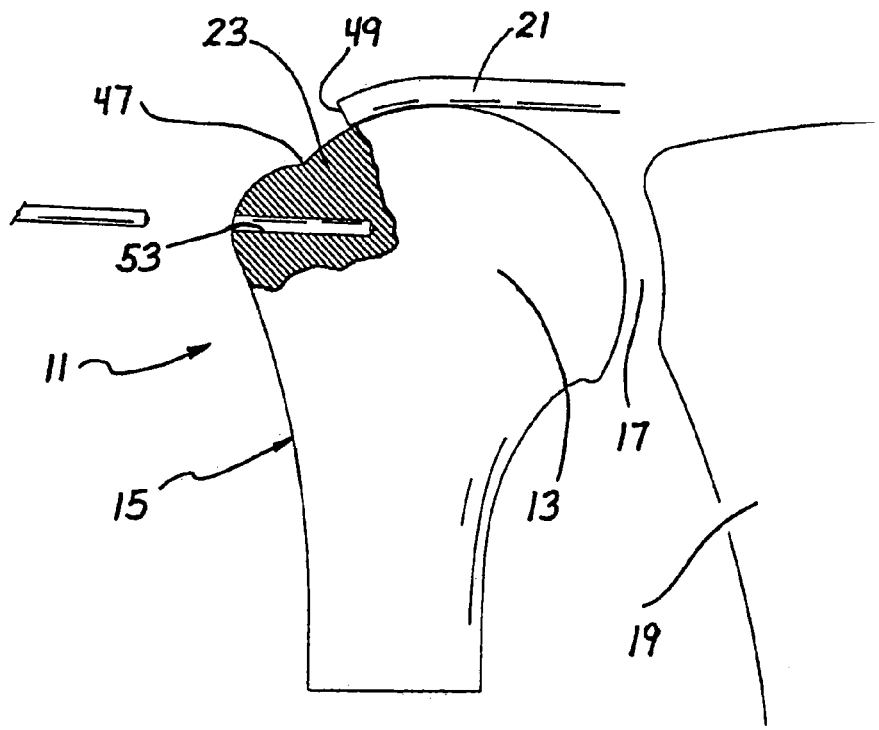
FIG. 1 illustrates a humerus in partial cross-section, and a tendon, which together form part of a rotator cuff to be repaired, wherein a hole has been made in the humerus for accommodating a suture anchoring device which is constructed in accordance with the principles of the present invention.

Referring now more particularly to the drawings, there is shown in FIG. 1 a portion of a partially torn rotator cuff 11. In the illustration, which is simplified for purposes of clarity, a globular head 13 of a humerus 15 is disposed in a glenoid cavity 17 formed by a scapula 19. A supraspinatus tendon 21, the end of which is normally fully attached onto a facet of a greater tuberosity 23, is shown in a detached condition, resulting in a diagnosis that the rotator cuff has been torn.

Now with particular reference to FIGS. 7 and 8, there is illustrated one preferred embodiment of a knotless suture anchoring device 25 constructed in accordance with the principles of the invention. In its preferred configuration, the anchoring device 25 comprises a hollow stem or shaft 27, having a longitudinal axis 28 and a periphery. A pair of longitudinal slits 29 extend along a portion of a distal section of the shaft 27 from its distal end 31, and a wider and shorter recess 32 may also be disposed on the shaft distal end 31, as shown. At the shaft's proximal end, there is disposed a hexagonal nut 33, which is adapted to receive and engage an anti-rotation cap 35 onto it, for purposes to be described below. The anti-rotation cap 35, in this embodiment, has an internally disposed hexagonal surface 36 which corresponds with the hexagonal nut 33 to permit a snug fit. An internal lumen 37, which extends through both the shaft 27 and the hexagonal nut 33, is adapted to receive suturing material 39, as shown in FIG. 7.

The anti-rotation cap 35 includes a radially extending flange portion 41, which preferably has a flap member 43 disposed thereon. The purpose of the anti-rotation cap 35 is to prevent rotation of the anchoring device 25 about its axis once it has been inserted into, for example, the humeral bone of a patient, as will be described. The purpose of the flap member 43, which extends angularly outwardly from the flange surface, as shown, is to prevent axial migration of the device, once in position, as will also be explained. The flap member 43 may be oriented at any desired angle, which may be either fixed or adjustable.

An alternative embodiment of the invention is illustrated in FIG. 9, wherein like elements to those depicted in FIGS. 7 and 8 are designated by like reference numerals, increased by 100. Thus, there is shown a knotless suture anchoring device 125 which is substantially identical to anchoring device 25 shown in FIGS. 7 and 8, except that the internal surface 45 of the anti-rotation cap 135 is ribbed, rather than being hexagonal. The effect of the ribs on the surface 45 is similar to that of the internal hexagonal surface 36 of the cap 35, namely, to provide a snug engagement between the anti-rotation cap 135 and the nut 133. Other suitable configurations for both the cap 35, 135 and the nut 33, 133 may, of course, be utilized as well.

A preferred surgical technique for suturing the tendon 21 to the humeral head 13 will now be described, with particular reference to FIGS. 1-6b and 19. Initially, the preferred technique proceeds in accordance with conventional arthroscopic techniques for rotator cuff repair, in that access or working ports are positioned in the shoulder in a conventional fashion. An endoscope is inserted through one of the access ports, and, once the endoscope is in place and functional, the rotator cuff tear is observed, and the site is prepared. Site preparation steps include preparing the bone surface by creating a notch or rough surface 47 in the humeral head 13 for accommodation of the detached or torn end 49 of the tendon 21, and to encourage reattachment to the bone 15. Then, suturing material 39 is introduced through a working port to the surgical site, and one end or both ends thereof is/are attached to the detached end 49 of the tendon 21. The type of stitch 51 (FIGS. 6, 6a, 6b, and 19) which is employed, and the type of suturing instrument, if any, which is utilized to perform the suturing step just described is beyond the scope of the invention. A number of different suturing techniques and devices are well known in the prior art for this type of surgical application, and any one of them could be appropriate. For example, a "mattress" stitch or a "Mason-Allen" stitch could be employed, if desired, and a preloaded suturing instrument for assisting in the suturing step could also be employed, depending upon the surgeon's preference.

Figure 3:
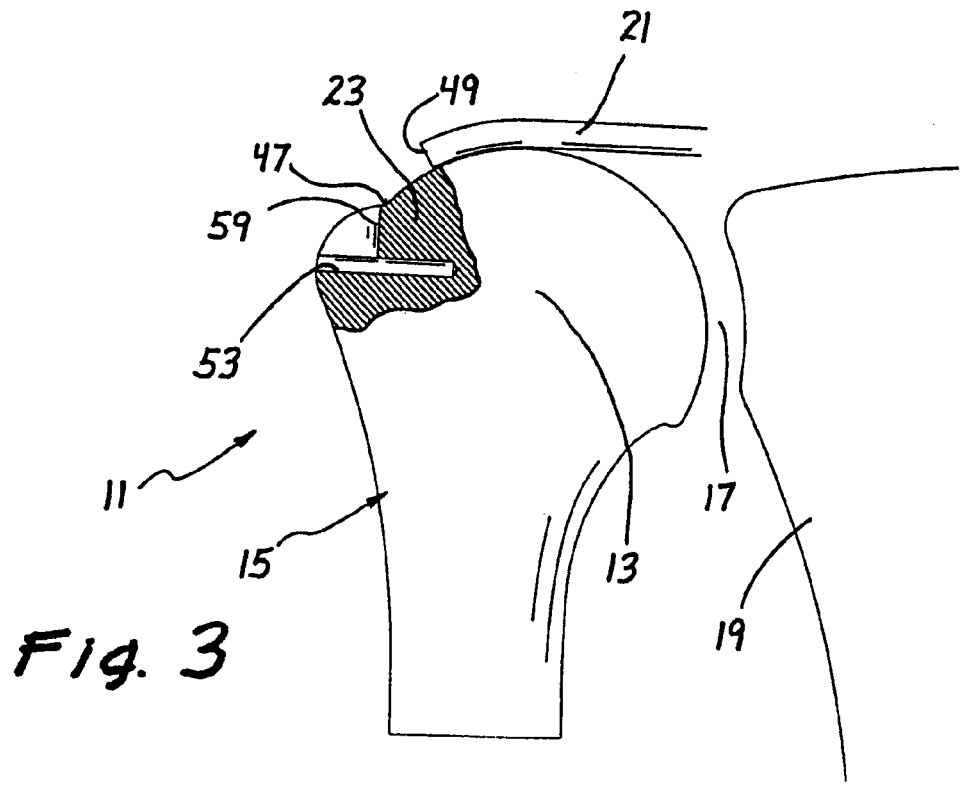
FIG. 3 is a view similar to FIGS. 1 and 2 illustrating the humerus after the slit has been completed.
Figure 2:
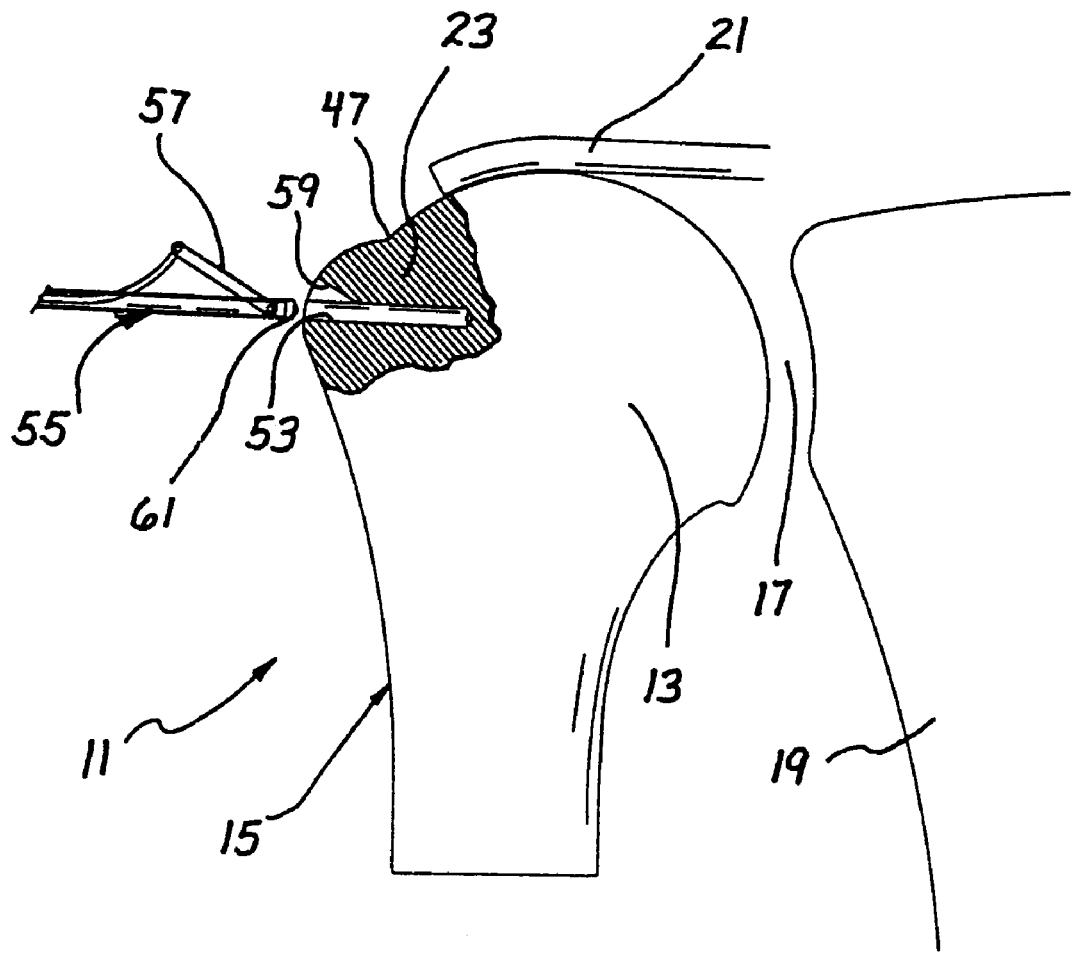
FIG. 2 is a view similar to FIG. 1 illustrating a step in the inventive procedure wherein a slit is made in the humerus.
Figure 2A:
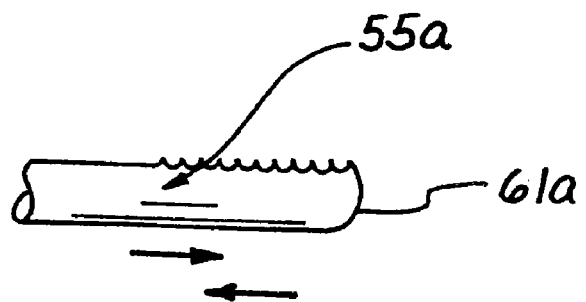
FIG. 2a is a schematic view of a portion of the device shown in FIG. 2, illustrating a sawblade which may be used to form the slit.

Once the tendon 21 has been sutured, a hole 53 (FIGS. 1-6) is strategically created at the greater tuberosity 23 of the humerus 15. It should be noted, at this juncture, that the inventive method does not require the torn end 49 of the tendon 21 to be sutured prior to the creation of the hole 53. The hole 53 could just as easily be created first, followed by the aforementioned suturing step. The hole 53 may be created using known techniques. For example, the hole 53 could be created using a drill. At this point, in one preferred method, as illustrated in FIG. 2, a saw 55 having a blade 57, which may reciprocate, if desired, is introduced axially into the hole 53, and manipulated so that the blade 57 cuts a slit 59 (FIG. 4) into the bone 15, extending from the hole 53 to the upper edge of the humeral head 13 (see FIG. 3). The saw 55 may be of any known construction. An alternative straight-bladed saw 55a is illustrated in FIG. 2a, for example. The slit 59 is cut deeper into the bone as the saw 57 is advanced further into the hole 53, by suitable manipulations of the saw, until a distal end 61 of the saw 57 reaches the terminus 63 of the hole 53. When the slit-forming step is completed, the deep edge of the slit 60 should extend to the edge of the globular head 13 in a direction substantially orthogonal to the orientation of the hole 53, along the anticipated suture path between the tendon 21 and the anchoring device 25, as shown in FIGS. 3 and 6, which are cross-sectional views through the slit 59.

The slit 59 extends upwardly all the way to the edge of the globular head 13, and runs continuously along the surface of the greater tuberosity 23 from the hole 53 to the notch 47. The open edge of the slit 59 along the greater tuberosity surface is uniquely advantageous, because it permits a convenient, direct passageway through the bone 15 between the detached end 49 of the tendon and the anchoring device 25, to thereby permit anchoring of the free end of the suturing material 39 (that end which is not sutured to the detached end 49 of the tendon) to the bone 15, as will be described below. Furthermore, once the tendon 21 is anchored in place, the slit 59 is sufficiently narrow that it quickly heals closed, so that there is no opportunity for the suturing material 39 to migrate out of the slit through the open upper edge.

After the slit 59 has been created, the free end or ends of the suturing material 39 is secured to the anchoring device 25 by holding it against the shaft 27 and rotating the shaft several times, thereby wrapping a portion of the length of suturing material 39 around the periphery of the shaft 27. A preferred approach is to first slide the shaft 27 along the free end of the suturing material 39 so that the material 39 runs through the lumen 37, as shown in FIG. 7. Then, as the shaft 27 is rotated, to begin wrapping an additional length of the suturing material externally thereabout, the longitudinal slits 29 permit the distal end 31 of the shaft to be radially compressible responsive to the pressure of the suturing material being wrapped about the distal end, causing the outer walls of the shaft 27 at the distal end 31 to be reduced in diameter sufficiently to engage the suturing material 39 which is passing through the internal lumen 37. This engagement or clamping effect is useful in helping to prevent the axial migration of the suturing material 39 through the internal lumen 37 over time, further increasing the reliability of the inventive device.

Figure 6:
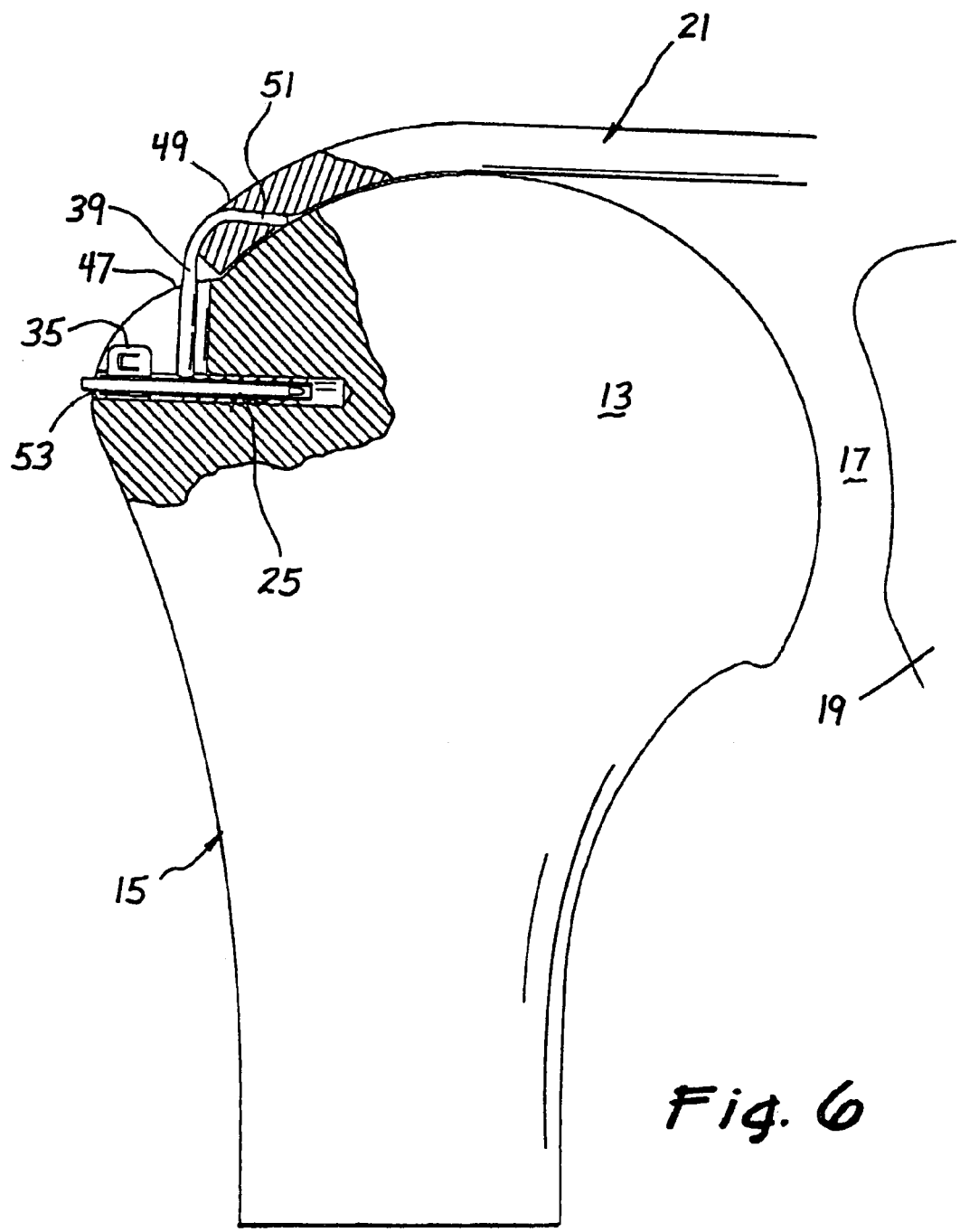
FIG. 6 is a partial cross-sectional view similar to FIGS. 1-3 illustrating the humeral head and tendon after they have been sutured together using the apparatus and methods of the present invention.

After a few turns, but while the length of suturing material 39 extending from the tendon 21 to the anchoring device 25 is still slack, the anchoring device 25 is inserted into the hole 53, as shown in FIGS. 6 and 6*a*. It should be noted that the inventive method is sufficiently broad to permit variation in the order in which these described steps are performed. For example, the anchoring device 25 may be inserted into the hole 53 prior to beginning the wrapping process by rotating the shaft 27, with the wrapping of the suturing material 39 about the shaft 27 taking place only after the anchoring device 25 has been placed inside the hole 53.

In the preferred method, the anchoring device 25 is advanced sufficiently far into the hole 53 so that the length of suturing material 39 which is not wrapped about the shaft 27 or passing through the lumen 37 runs along the deep edge of the slit 59, as shown in FIGS. 6 and 6*a*. Then, the shaft 27 is rotated through several additional revolutions, wrapping additional loops of suturing material 39 thereabout, until the torn tendon end 49 is drawn snugly against the bone 15, and the length of suturing material 39 extending through the slit 59 is taut. The inventors have discovered that an additional benefit of the present inventive design is that, as the shaft 27 is rotated within the hole 53, the portion of suturing material 39 which is wrapped about the shaft 27 acts to "thread" the soft cancellous bone which comprises the internal surface of the hole 53, thereby providing an additional means for securing the anchoring device 25 within the hole 53, and preventing unwanted axial migration thereof.

When the suturing material 39 has been wrapped sufficiently about the shaft 27 to secure the tendon 21 to the bone 15, the anti-rotation cap 35 is installed onto the proximal end of the anchoring device 25, as illustrated in FIGS. 7 and 7*a*. As shown, a preferred method for doing this is to slide the cap 35 distally along the length of suturing material 39 which extends proximally from the shaft lumen 37, until the cap 35 is engaged with the nut 33; i.e. slid coaxially thereover. For the FIGS. 7 and 7*a* embodiment, this involves aligning the internally disposed hexagonal surface 36 of the cap 35 with the exterior surface of the hexagonal nut 33, and then sliding the cap 35 axially onto the hexagonal nut 33, creating a slight interference fit to prevent disengagement. For the FIG. 9 embodiment, the procedure involves sliding the cap 135 axially over the nut 133, and allowing the ribbed interior surface of the cap 135 to create an interference fit with the exterior surface of the nut 133. As illustrated in FIGS. 6 and 6*a*, the flange portion 41 of the anti-rotation cap 35 slides axially into the slit 59, which will ultimately then close around it, retaining it in a fixed position, as the remaining cylindrical portion of the cap 35 slides axially into the hole 53.

Functionally, when the anti-rotational cap 35 and associated flange portion 41 are in position on the anchoring device 25, as shown in FIGS. 6 and 6*a*, the anchoring device 25 is prevented from rotating because of the lodgment of the flange portion 41 in the slit 59. This prevents the device from being inadvertently "backed out" of the hole 53, or the suturing material 39 from being inadvertently unwrapped (partially or fully) from its disposition about the shaft 27, either during the course of the procedure or afterwards.

In the preferred embodiment, as discussed above, the flange portion 41 of the anti-rotational cap 35 includes a flap member 43, which is angularly displaced relative to the plane of the flange member. This flap member 43 functions to engage the bone surrounding the hole 53, and to thereby assist in preventing undesired axial displacement of the anchoring device 25 proximally out of the hole 53. In other words, it functions as an anchor to axially hold the shaft 27 in place, once it has been installed to a desired position within the hole 53.

The above described anti-rotation cap 35, 135, as shown in alternative embodiments in FIGS. 7-9, is just one preferred approach for preventing undesired rotation of the anchoring device 25, 125 once the device has been inserted into the bone 15. Many other alternative anti-rotation systems could be employed as well. For example, in FIGS. 14-15, there is shown an alternative embodiment for such an anti-rotation system. In this embodiment, wherein like elements to those in FIGS. 7 and 8 are designated by like reference numerals, increased by 200, an anti-rotation bar 65 is employed, rather than the anti-rotation cap 35 earlier described. The procedure for inserting the anchoring device 225 into the bone 15 is the same as that for inserting the devices 25 and 125, except that, after the suturing material 239 has been wrapped about the shaft 227 a sufficient number of revolutions to secure the tendon 21 to the bone 15, and to ensure that the anchoring device 225 will not inadvertently separate from the suturing material 39, the anti-rotation bar 65 is installed onto the proximal end of the device 225. As with the FIG. 7 embodiment, a hexagonal nut 233 is disposed on a proximal end of the shaft 227. However, in the FIG. 14 embodiment, the nut 233 includes a recess or slot 67 at its proximal end for the purpose of accommodating the anti-rotation bar 65. To prevent undesired rotation of the shaft 227, the anti-rotation bar 65 is inserted into the recess 67, after the device 225 has been inserted into the hole 53. One end of the anti-rotation bar 65 will be inserted into a portion of the slit 59 as the bar 65 is inserted into the recess 67, in a manner similar to that by which the flange portion 41 is inserted into the slit 59 in the FIG. 7 embodiment. A second slit or recess, opposed to the first slit 59, and of sufficient size to accommodate the second end of the bar 65, may be formed in the bone 15, either by the prior use of suitable forming equipment, such as a saw, in a manner similar to that by which slit 59 is created, or by forcing (i.e. pounding) the second end of the bar 65 into the soft cancellous bone 15 surrounding the hole 53.

Figure 14:
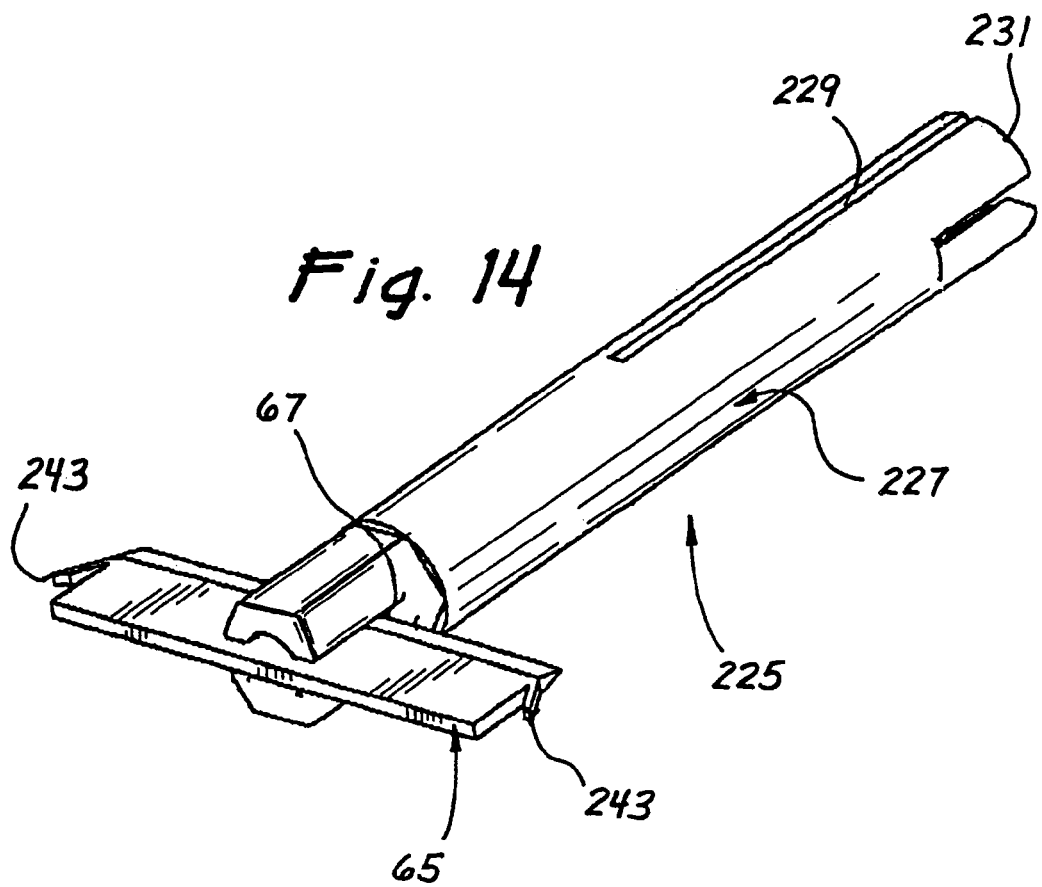
FIG. 14 is a perspective view similar to FIG. 8, of a modified embodiment of the knotless suture anchoring device constructed in accordance with the principles of the present invention, wherein an anti-rotation bar is employed rather than an anti-rotation cylinder.
Figure 15:
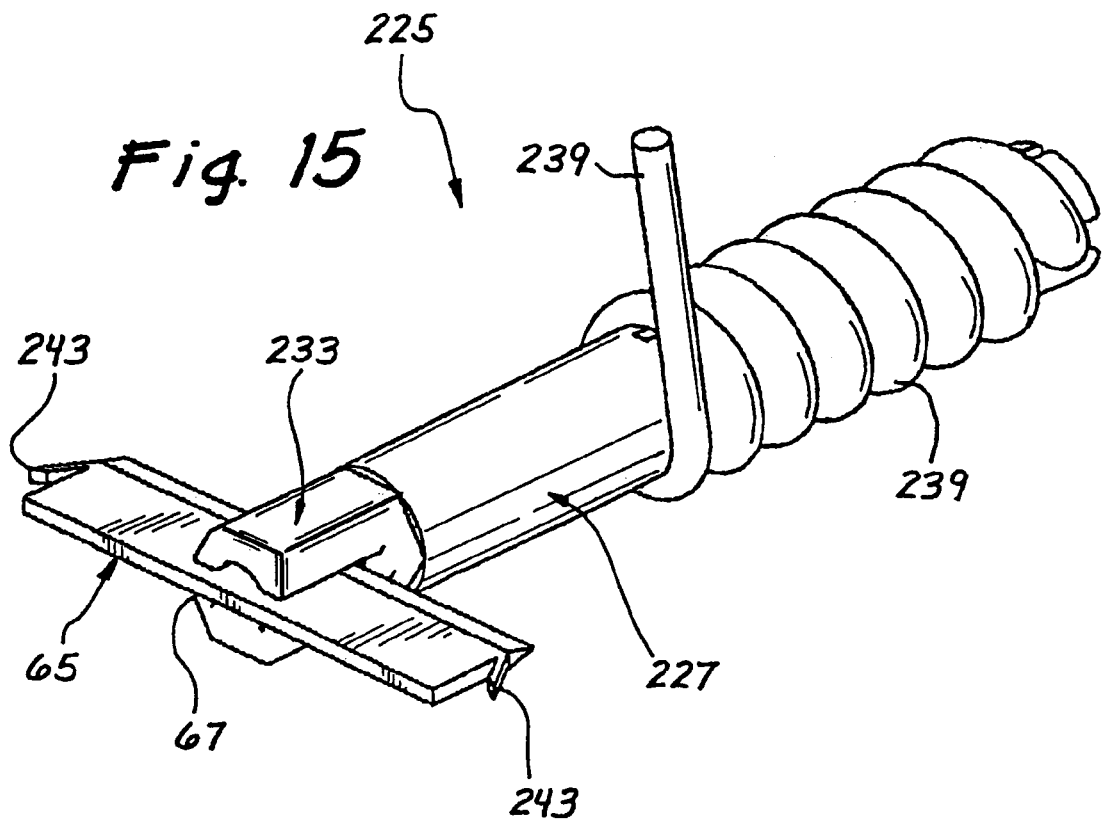
FIG. 15 is a perspective view of the embodiment illustrated in FIG. 14, wherein suturing material has been wrapped therearound.

Functionally, when the anti-rotational bar 65 is in position on the anchoring device 225, as shown in FIGS. 14 and 15, the anchoring device 225 is prevented from rotating because of the lodgment of the anti-rotation bar 65 in the slit 59. This prevents the device from being inadvertently "backed out" of the hole 53, or the suturing material 239 from being inadvertently unwrapped (partially or fully) from its disposition about the shaft 227, either during the course of the procedure or afterwards.

In the preferred embodiment, the anti-rotation bar 65 includes one or more flap members or barbs 243, each of which are angularly displaced relative to the plane of the anti-rotation bar. These flap members functions to engage the bone surrounding the hole 53, and to thereby assist in preventing undesired axial displacement of the device 225 proximally out of the hole 53.

Of course, other anti-rotation configurations, including, for example, radially deployable structure which is always present on the shaft 27, 127, 227, which will act to rotationally lock the shaft in place may be employed, to the same effect.

Figure 10A:
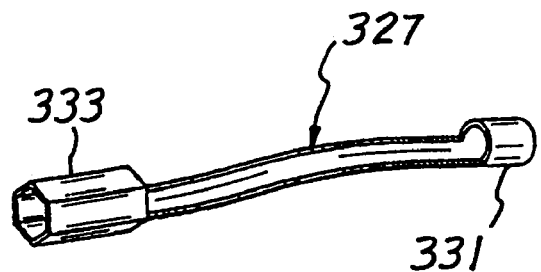
FIG. 10a is a perspective, schematic view of a modified embodiment of the distal portion of the inventive knotless suture anchoring device.
Figure 10B:
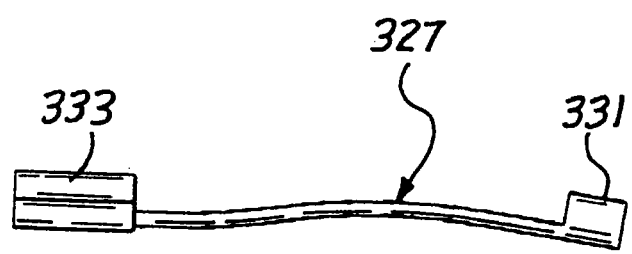
Figure 10C:
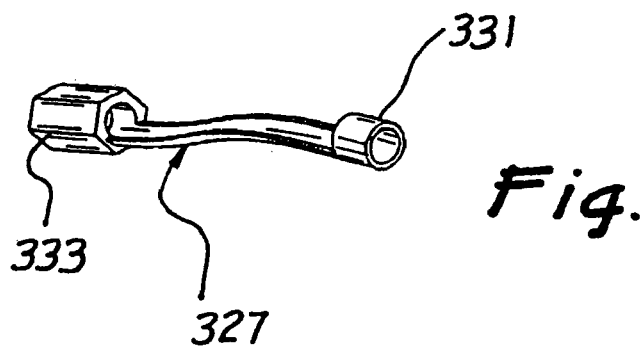

Many alternative embodiments of the inventive anchoring device may be employed within the scope of the inventive concept. For example, FIGS. 10*a*-10*c*, wherein like elements to those shown in FIGS. 1-8 are designated by like reference numerals, increased by 300, illustrate a modified embodiment of a shaft portion 327 of the anchoring device, wherein the shaft 327 is of an open construction along its midsection, and has a curved configuration as well. The curved configuration of the shaft 327 in some circumstances may assist in equalizing the forces applied on the device 25 once the suturing material 39 has been wrapped about the shaft 327 by ensuring that substantially the entire surrounding internal wall of the hole 53 contacts the wrapped shaft 327 at some point along its length. This may improve the ability of the shaft 327 to resist undesired axial movement once the tendon 21 is properly attached to the bone 15 and the medical procedure is completed.

Figure 11A:
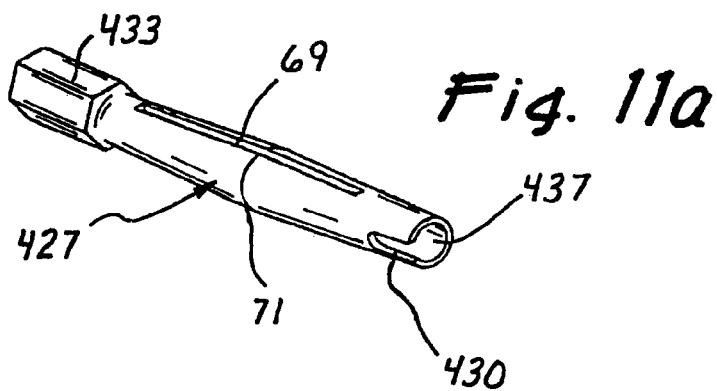
FIG. 11a is a perspective view of another modified embodiment of the distal portion of the inventive knotless suture anchoring device, wherein the shaft thereof includes two longitudinal slits.
Figure 11B:
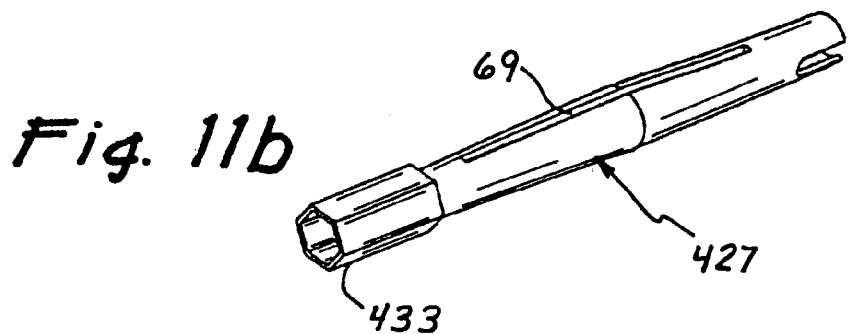

FIGS. 11*a*-11*b* illustrate another alternative embodiment of the inventive device, wherein like elements to those shown in FIGS. 1-8 are designated by like reference numerals, increased by 400. In this embodiment, the shaft 427 is constructed to have two longitudinal slits 69 (only one is shown—the second slit is diametrically opposed to the visible one) disposed along a midportion thereof, as illustrated, and the outer diameter of the shaft 427 is bowed radially outwardly at a centerpoint 71 of the shaft 427, relative to its diameter at each end. The slits 69 are substitutes for the slits 29 shown in FIGS. 7 and 8, and differ from slits 29 because their distal ends terminate proximally of the distal end of the shaft 427. Though not shown, it is noted that the inner diameter of the lumen 437 of the shaft 427 is preferably substantially constant along its entire length.

In operation, as the suturing material 39 is wrapped about the shaft 427, the slits 69 function to permit the diameter of the shaft 427 to be compressed at its centerpoint and adjacent regions on either side thereof, where the outside diameter is bowed outwardly, by the suturing material. Since the inner diameter is constant, this causes the inner diameter at the centerpoint to be compressed so that it is less than the inner diameter near either end of the shaft 427, thereby causing the interior lumen walls to contact and compress the suturing material passing through the lumen 437 near the axial centerpoint of the shaft 427. This contact assists in resisting undesirable axial migration of the suturing material through the lumen.

Figure 12A:
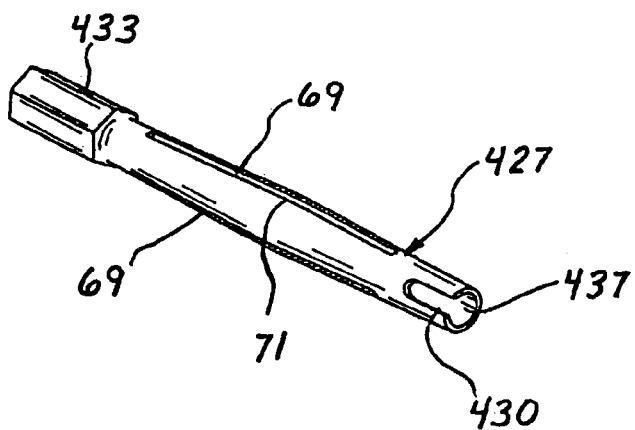
FIG. 12a is a perspective view of yet another modified embodiment of the distal portion of the inventive knotless suture anchoring device, wherein the shaft thereof includes three longitudinal slits.
Figure 12B:
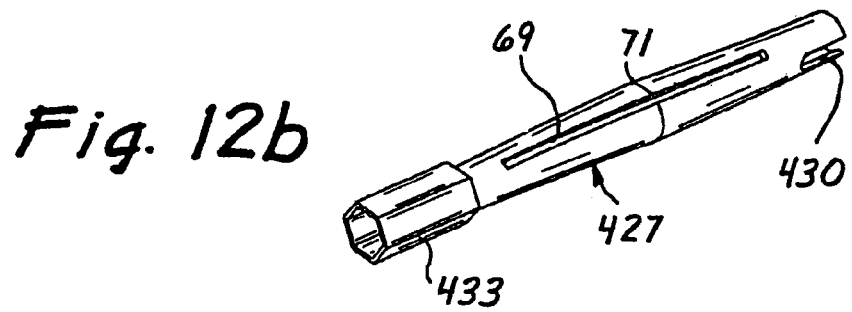

FIGS. 12*a* and 12*b* illustrate an embodiment identical to that of FIGS. 11*a* and 11*b*, except that in the FIGS. 12*a* and 12*b* embodiment, three slits 69 are employed rather than two. In actuality, any number of slits 69 may be employed to obtain the inventive results which are described above.

Figure 13:
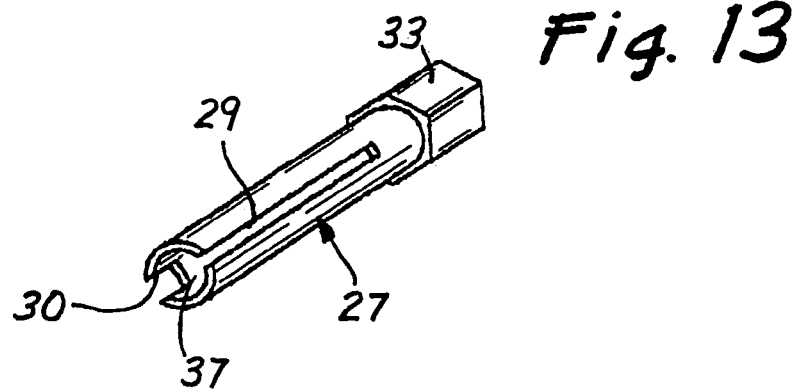
FIG. 13 is a perspective view of yet another modified embodiment of the distal portion of the inventive knotless suture anchoring device, wherein the shaft thereof includes only one longitudinal slit.

FIG. 13 illustrates an embodiment similar to that of FIGS. 7 and 8, and for that reason like elements are designated by like reference numerals. The only substantive difference between the two embodiments is that in the FIG. 13 embodiment only one longitudinal slit 29 is employed, instead of two. In actuality, any number of slits 29 may be employed, as long as they function to cause the inner diameter of the shaft 27 to be reduced as a result of compression applied by the wrapped suturing material, thereby cinching the lumen walls down onto the suturing material disposed in the lumen 37 to clamp same in place.

Figure 16:
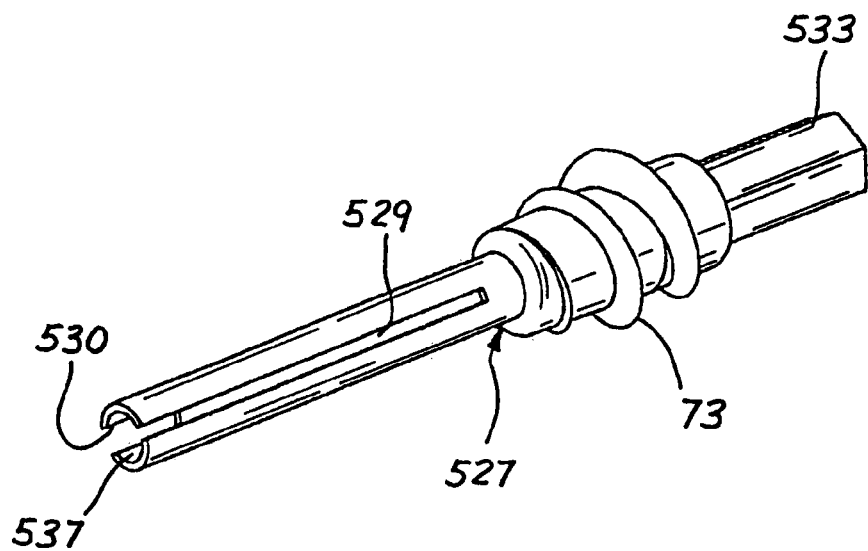
FIG. 16 is a perspective view of another modified embodiment of the distal portion of the inventive knotless suture anchoring device, wherein the shaft includes one longitudinal slit and a portion of the shaft is threaded.
Figure 17:
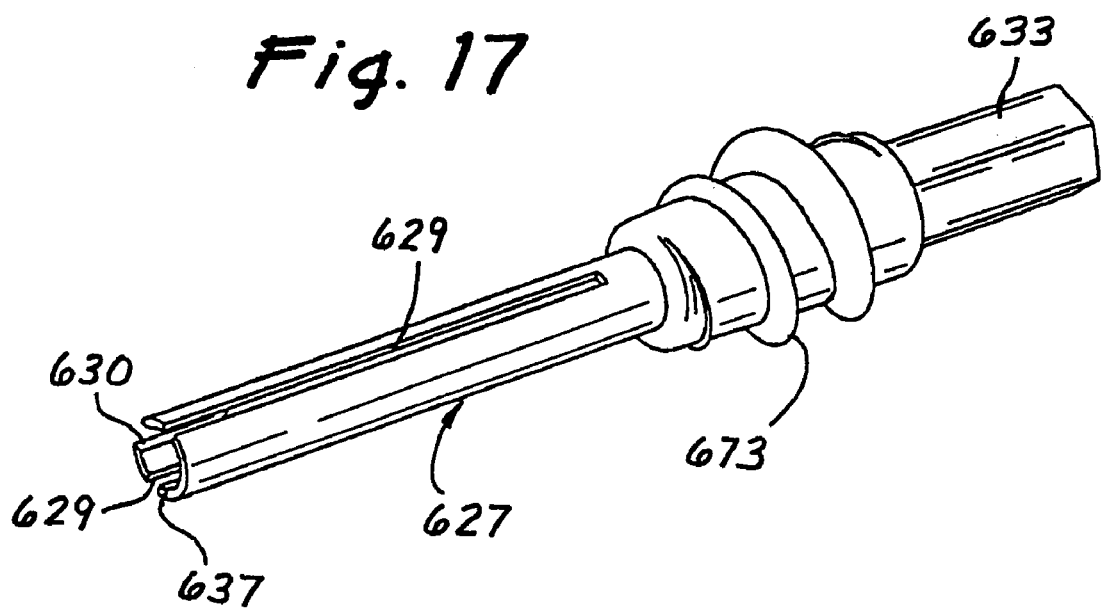
FIG. 17 is a perspective view of another modified embodiment of the distal portion of the inventive knotless suture anchoring device, wherein the shaft includes two longitudinal slits, and a portion of the shaft is threaded.
Figure 18:
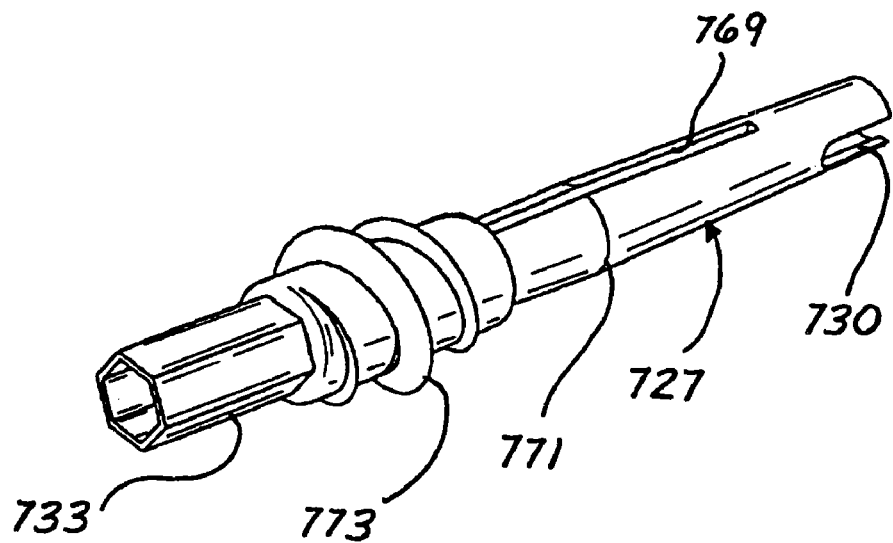
FIG. 18 is a perspective view of another modified embodiment of the distal portion of the inventive knotless suture anchoring device, wherein the shaft includes three longitudinal slits, and a portion of the shaft is threaded.
Figure 19:
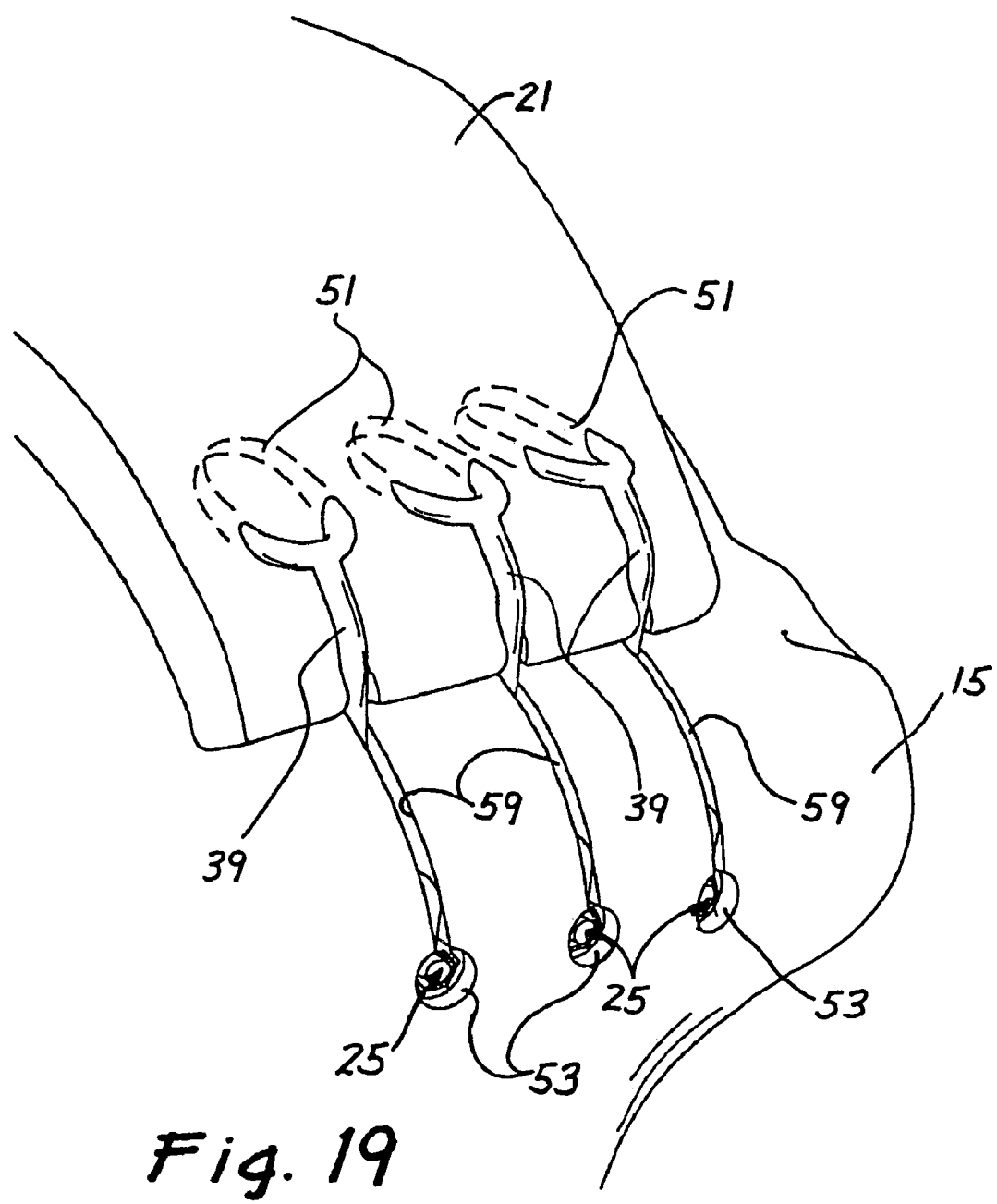
FIG. 19 is a perspective, schematic view of the point of attachment between a patient's humeral head and the end of the tendon to be re-attached thereto, in accordance with one method taught herein.

FIGS. 16-18 illustrate three different modified embodiments of the shaft of the inventive anchoring device, wherein like elements to those shown in previously described embodiments are designated by like reference numerals, preceded by the numerals 5, 6, and 7, respectively. FIG. 16 illustrates an embodiment very similar to that of FIG. 13, except for the addition of external threads 73, disposed on the shaft 527 proximally of the slit 529. The function of the FIG. 16 embodiment is identical to that of the FIG. 13 embodiment, with a single slit 529, except that the threads 73 create a threaded engagement with the bone 15 forming the internal walls of the hole 53, as the shaft 527 is rotated to wrap the suturing material therearound. As described supra, the wrapped suturing material creates a threaded engagement itself with the soft cancellous bone in the humeral head 13, but the employment of external threads 73 significantly enhances the effect, and provides a further mechanism for resisting unwanted axial pull-out of the anchoring device 25 from the hole 53.

FIG. 17 illustrates an embodiment very similar to that of FIGS. 7 and 8, with two longitudinal slits 629, except for the addition of external threads 673, which function in the manner above described with respect to threads 73 in FIG. 16.

FIG. 18 illustrates an embodiment very similar to that of FIGS. 11*a*, 11*b*, and 12, employing one or more longitudinal slits 769 along a central portion of the shaft 727, and functioning in a manner identical to that described supra in connection with the FIGS. 11*a*, 11*b*, and 12 embodiments, except for the addition of external threads 773. These threads function to create an enhanced threaded engagement with the surrounding bone 15, as above described.

Figure 20A:
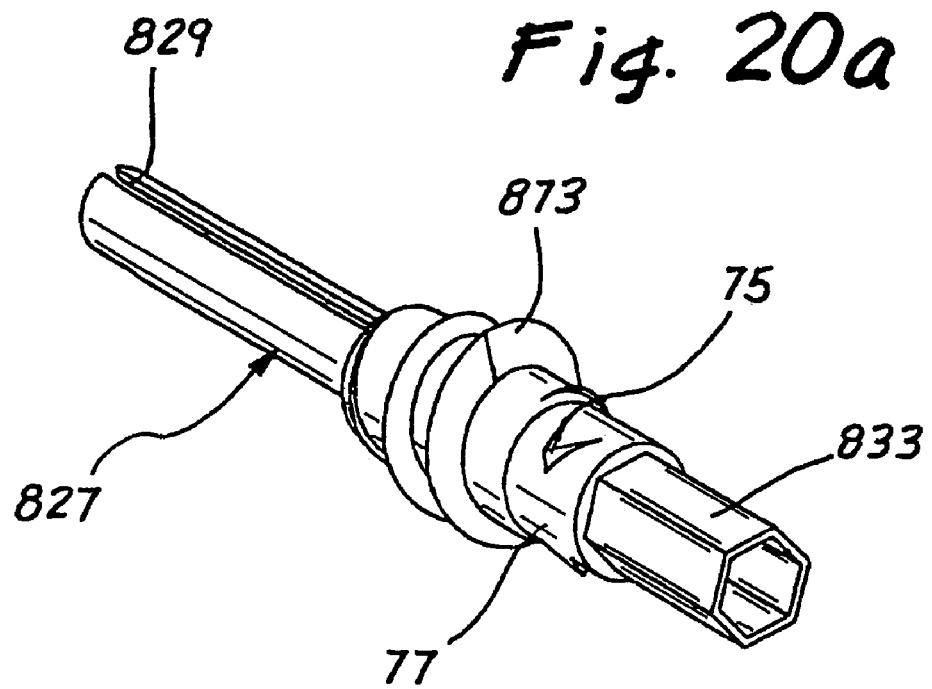
FIG. 20a is a perspective view of another modified embodiment of the distal portion of the inventive knotless suture anchoring device, wherein the shaft includes anti-rotation barbs and a portion of the shaft is threaded.
Figure 20B:
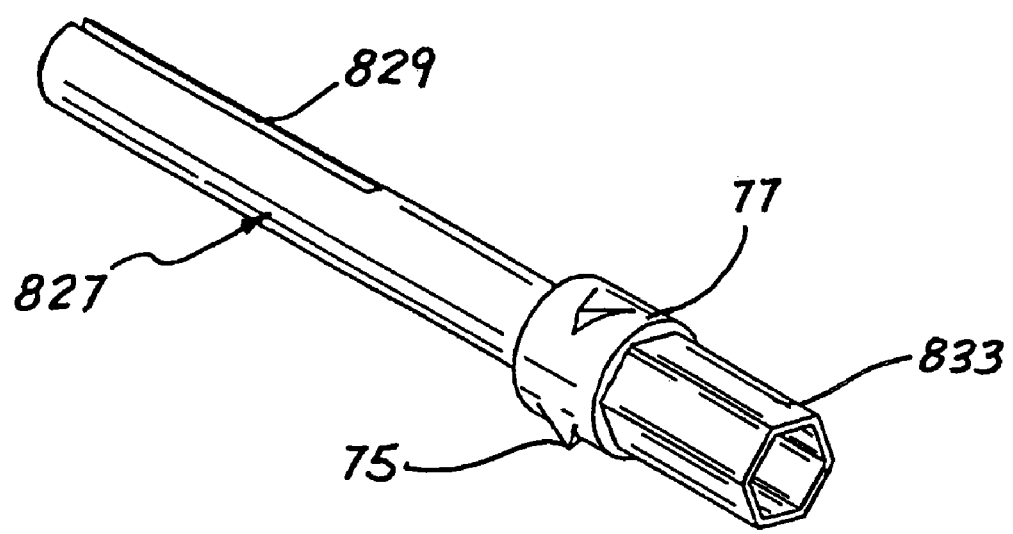
FIG. 20b is a perspective view similar to FIG. 20a, wherein the shaft includes anti-rotation barbs but there are no threads.

FIGS. 20*a* and 20*b* illustrate embodiments similar to those illustrated in the above described figures, wherein like elements are designated by like reference numerals, preceded by an 8. Thus, the embodiment shown in FIG. 20*a* functions in a manner essentially identical to that of the embodiment shown in FIG. 16 or 17, except that anti-rotational barbs 75 have been added on the circumference of the shaft 827, in order to provide an additional impediment to undesired rotation of the shaft 827 once it has been inserted into the hole 53 and has been wrapped by the suturing material 39. FIG. 20*b* also functions in a similar manner, but does not include external threads 873. In the preferred embodiments, the barbs 75 are disposed on a collar 77, though other arrangements may be suitable as well. It is noted that, depending upon a number of factors, including the desired application, differing combinations of anti-rotational mechanisms may be employed. FIG. 20*b* represents an embodiment where the external threads 873 shown in FIG. 20*a* are not deemed to be necessary to achieve adequate anti-rotational performance. Either of the embodiments shown in FIGS. 20*a* and 20*b* may be employed with or without additional anti-rotational mechanisms, such as those shown in FIGS. 7-9.

Figure 21A:
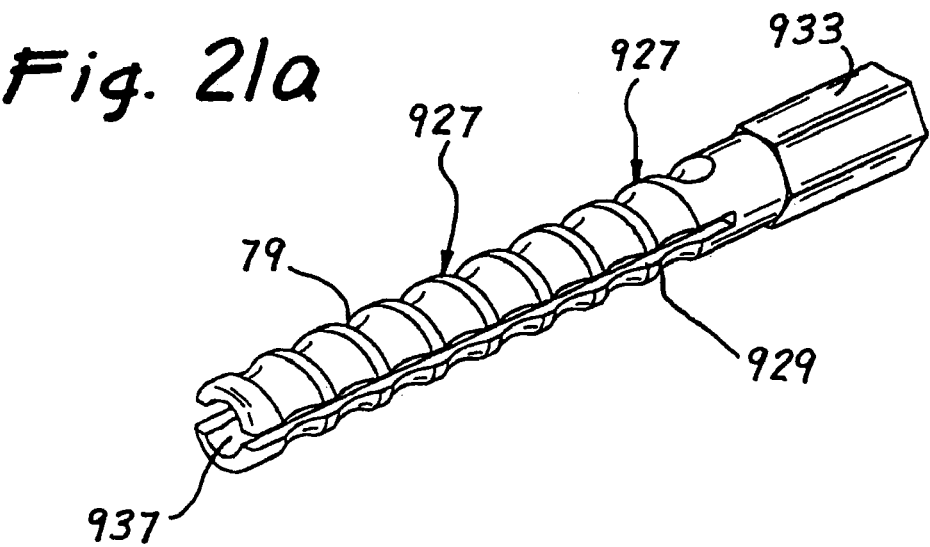
FIG. 21a is a perspective view of another modified embodiment of the distal portion of the inventive knotless suture anchoring device, wherein the shaft includes guiding ridges for the suturing material to track in as it is wrapped thereabout.
Figure 21B:
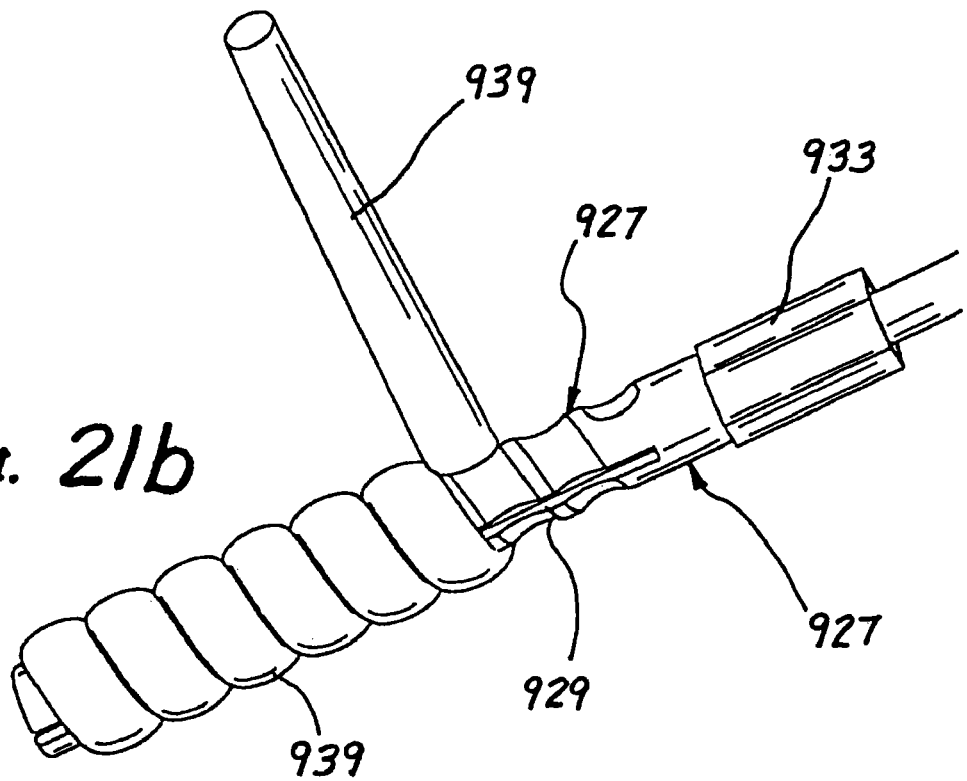
FIG. 21b is another perspective view of the embodiment illustrated in FIG. 21a, which shows suturing material wrapped about the shaft thereof.

FIGS. 21*a* and 21*b* illustrate a further modified embodiment, wherein like elements to those of prior described embodiments are denoted by like reference numerals, preceded by the numeral 9. This embodiment functions in a manner substantially identical to that of the embodiment of FIGS. 7 and 8, for example, except that in this embodiment the external surface of the shaft 927 has been fabricated to include a spiral groove 79 which extends along the length of the shaft 927 for the purpose of guiding the suturing material 929 as it is wrapped about the shaft.

FIGS. 22*a*-22*c* illustrate still another modified embodiment, wherein like elements to those of prior described embodiments are denoted by like reference numerals, preceded by the numeral 10. In this embodiment, the shaft 1027 is partially open, comprising only a hemispherical section through a portion of its length, as shown in FIGS. 22*a* and 22*b*. Thus, as shown particularly in FIG. 22*b*, the portion of the suturing material 1039 which lies axially along the open portion of the shaft 1027 is exposed to the outside of the shaft, as opposed to prior described embodiments wherein the suturing material 1039 extending through the shaft lumen is entirely enclosed by the shaft. Functionally, the result is that the outer wrap of suturing material 1039 is in direct contact with the suturing material extending through the center of the shaft, thereby acting to impede undesired axial migration of the suturing material 1039 which extends axially along the shaft 1027.

Figures 23A, 23B, 23C:
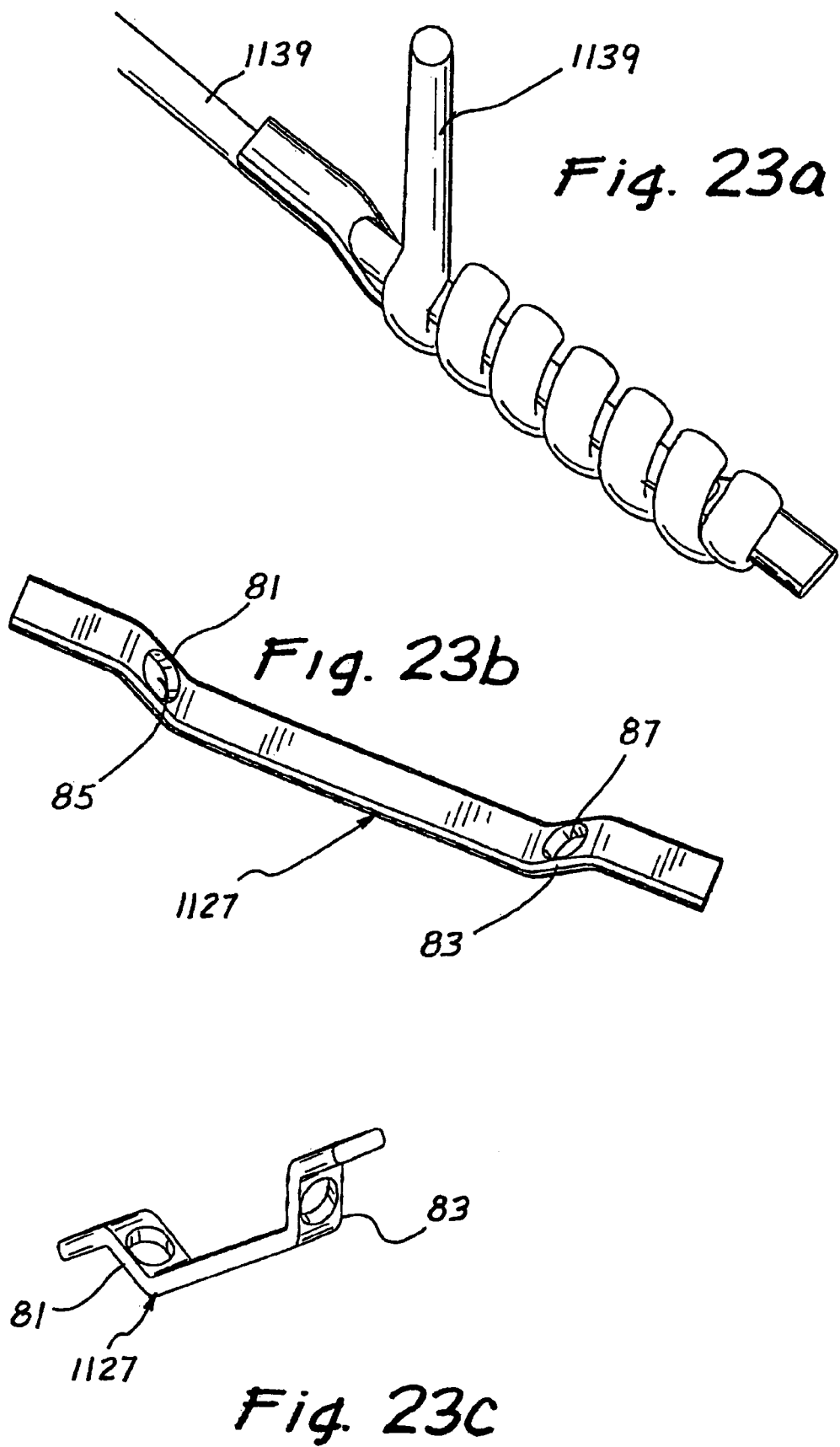
FIG. 23a is a perspective view showing yet another modified embodiment of the knotless suture anchoring device of the present invention, wherein the device comprises a flat bar.
FIG. 23b is a perspective view similar to FIG. 23a, with the suturing material removed for clarity.
FIG. 23c is another perspective view of the device shown in FIGS. 23a and 23b.

FIGS. 23*a*-23*c* illustrate yet another modified embodiment, wherein like elements to those of prior described embodiments are denoted by like reference numerals, preceded by the numeral 11. This embodiment is somewhat similar to that of FIGS. 22*a*-22*c*, in that in this embodiment the suturing material 1139 which extends along the center longitudinal axis of the shaft 1127 is also exposed, and the wrapped suturing material 1139 also directly contacts the center-lying suturing material in this embodiment. However, in this embodiment, the shaft 1127 comprises only a flat bar having two bend regions 81 and 83, respectively, in which are disposed first and second apertures 85 and 87, respectively. The apertures 85 and 87 function to receive the portion of suturing material which lies axially along the length of the shaft bar 1127, as shown in FIG. 23*a*.

FIGS. 24*a* and 24*b* show a further modified embodiment, wherein like elements to those of prior described embodiments are denoted by like reference numerals, preceded by the numeral 12. In this embodiment, the shaft 1227 is formed of a solid cylindrical biocompatible material. The external surface of the shaft 1227 includes a spiral groove 89, forming a series of peaks and valleys, over which the suturing material lies. First and second apertures 91 and 93, respectively, function to receive the suturing material 1239 at both ends of the shaft 1227 which includes the groove 89, and to channel it axially along the peaks and valleys created by the groove 89. The effect is to create a tortuous path for the suturing material which increases its resistance to axial slippage. Of course, alternative approaches may be taken to the creation of such a tortuous path along the external surface of the shaft 1227, without departing from the spirit of the present invention.

The inventors have found that the foregoing relatively simple techniques function remarkably better than prior art suture anchoring approaches to minimize the possibility that the anchor will pull out of the bone or that the suturing material will somehow become dislodged from the anchoring device during or after the shoulder repair procedure. Either of these occurrences, of course, jeopardizes the success of the procedure, and may result in the necessity of further repair of the rotator cuff. As shown particularly in FIGS. 5 and 19, in a preferred repair procedure, a plurality of suture anchoring devices 25 are inserted into a corresponding plurality of holes 53, adjacent to one another in the bone 15, in order to properly secure the tendon 21 to the bone 15. Although three adjacent holes 53 and associated anchoring devices 25 are shown, any number of anchoring devices (one or greater), may be employed, depending upon the particular case. If one or more of these anchoring devices were to fail, there is no feasible way to withdraw it from the bone, because of barbs which are disposed on the anchor to prevent its inadvertent withdrawal due to applied axial forces. Thus, it becomes useless, and another hole must be created, for the insertion of a new suture anchoring device. Each extra anchor weakens the bone, and reduces available "real estate" for possible future repair procedures.

An important reason for the vastly improved results afforded by the inventive procedure is that the tension placed on the suturing material by the tendon 21 is substantially normal or perpendicular to the axial direction of the anchoring device, so that the applied tension does not act to tend to pull the anchoring device axially out of the hole, as with prior art devices. Another reason is that, rather than merely being knotted to a suture eyelet on the anchoring device, as with many prior art devices, it is wrapped numerous times about the shaft of the anchoring device 25. This makes release of the suturing material 39 from the anchoring device 25 nearly impossible. In contrast, by anatomical necessity, the available prior art suture anchors are small, and all have a suture eyelet. Because the suture eyelet has a small radius, it concentrates stress on the suture at that point and creates a weak spot on the suture. In the inventive device, in contrast, the suture engagement radius is much larger, and is much less likely to impart stress on the suture.

Another important advantage of the present invention is the ability to control the tension on the suture. In existing devices, the tension on the suture is determined by how tightly or loosely the practitioner ties the securing knot on the suture eyelet. In contrast, in the inventive device, the tension is completely adjustable and may even be measured in torque-wrench fashion during the tightening process, if desired. The inventive device 25 has a substantial length of free suturing material wrapped about its shaft, as opposed to the very small length of suturing material which is knotted to the suture eyelet in prior art anchors. The increased length of suturing material 39 wrapped about the anchor shaft 27 of the present invention creates more compliance (slack) in the suturing material, and, thus, a much lower chance of failure. This compliance factor, in combination with the unique feature of the present invention, in that the tension applied to the anchor 25 by the suturing material attached to the tendon 21 is orthogonal to the axis of the anchor, rather than axial, reduces the risk of failure of the inventive anchor substantially.

Figure 4:
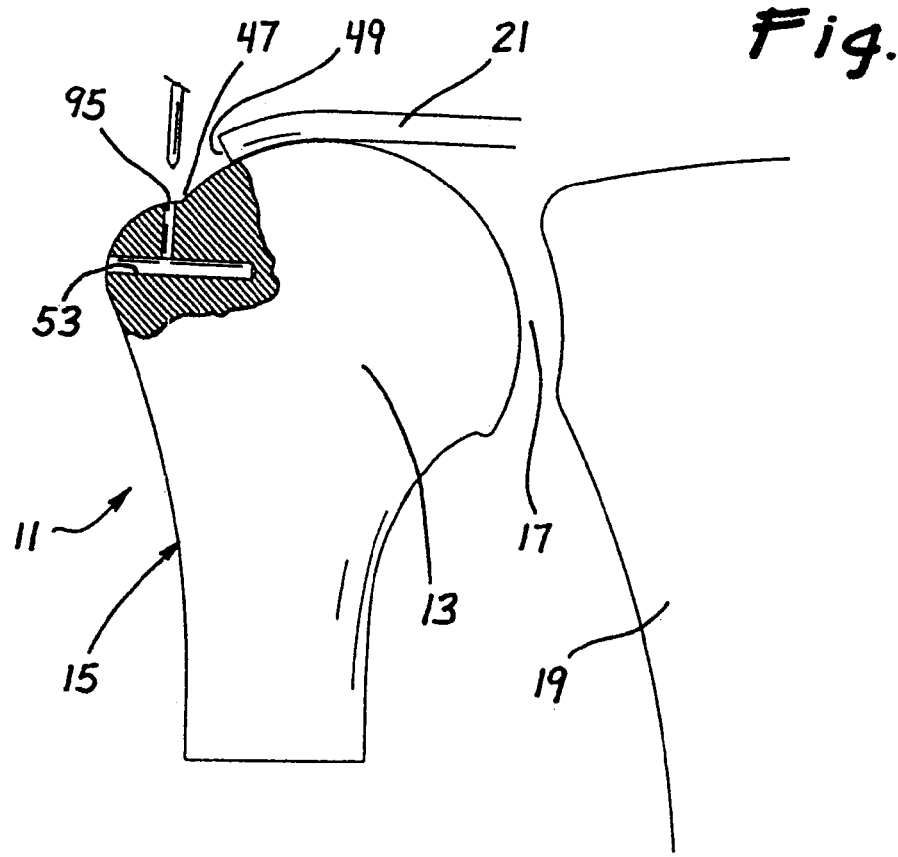
FIG. 4 is a view similar to FIGS. 1-3, illustrating an alternative procedure wherein a second hole orthogonal to the first hole is created in the humerus.
Figure 5:
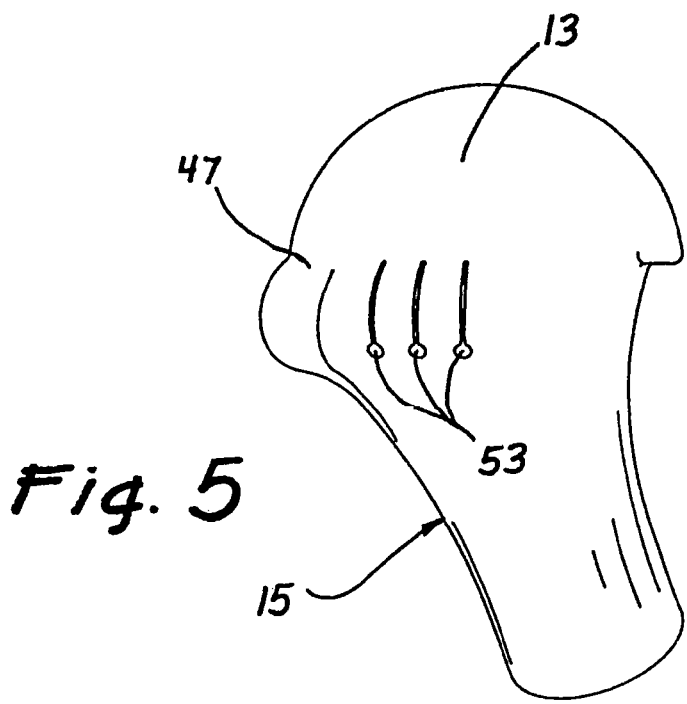
FIG. 5 is a perspective view of the humeral head, illustrating a preferred method wherein three parallel holes have been created therein.

In an alternative procedure, which may be preferred in some operating embodiments where space considerations are different than for rotator cuff procedures, once the tendon 21 has been sutured, and the hole 53 has been created, as described above, a transosseous tunnel 95 (FIG. 4) may be created, rather than a slit 59. The tunnel traverses the same path as the deep edge of the slit 60, as shown in FIG. 4, i.e. the anticipated suture path. Then, a suture snare device, such as are well known in the art, may be used to capture the free end of the suturing material 39, and to draw it through the transosseous tunnel 95 and into the hole 53. At the practitioner's option, the snare may be slid in either direction through the transosseous tunnel to capture the suturing material; i.e. the practitioner may elect either to snare the free end of the suture and then push it through the transosseous tunnel 95 into the hole 53, or to advance the snare down through the hole 53 and outwardly through the tunnel 95 until its distal end extends from the tunnel. The suture can then be captured with the distal end of the snare, and then pulled back through the tunnel 95 and the hole 53. Once the suturing material 39 has been captured and extends through the tunnel 95, the procedure concludes in a manner substantially identical to that of the previously disclosed method, wherein a free end of the suturing material is engaged with the anchoring device 25, preferably by sliding the device along a length thereof with that length of suturing material extending through the lumen 37. Then, the shaft is rotated to wrap several loops of suturing material therearound, taking advantage of rope friction effects to help to secure the suture, after which it is dropped into the anchor hole 53, the wrapping process is completed to snugly secure the tendon 21 to the bone 15, and the anchoring device is finally secured by one of the aforementioned anti-rotation devices.

Some of the advantages of the present invention can be summarized as follows:

1) The inventive anchoring device utilizes the principle of rope friction to secure the suturing material to the anchoring device. In other words, the present inventive configuration permits the contacting of the anchor device 25 with a substantial length of the suturing material (the portions either wrapped about the shaft or extending through the shaft lumen, for example), wherein that contact, because of frictional effects, functions to resist the axial migration of the suturing material relative to the anchoring device. Thus, no knots are required;

2) The inventive suture anchoring device does not include a suture eyelet. There is no requirement that a suture be passed through a small radius eyelet. Rather, the suture is wrapped around the entire shaft of the anchoring device, thereby increasing the radius of suture engagement with the anchoring device. As a result, in the inventive system, the suture is far less likely to break at the suture-to-anchoring device engagement point than in prior art systems;

3) No knots are required to secure the suturing material to the anchoring device. However, as shown in FIG. 6b, a knot 97 may be tied at the proximal end of the suturing material, if desired, in the inventive system, in order to provide even more assurance that the suturing material and anchoring device will not be separated;

4) The tension on the suture can be adjusted and even measured in the inventive system; and 5) An open slit may be employed for accommodating the suturing material connection between the bone anchoring device and the tendon 21, rather than the known transosseous tunnel.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention. In particular, it is noted that, while the procedure described relates to repair of torn rotator cuffs, the methods and devices disclosed are suitable for many other orthopedic application involving the re-attachment of connective tissue to bones.

What is claimed is:

1. A method for performing shoulder surgery to attach rotator cuff tissue to an adjacent bone at a target position, said method comprising:
   creating an opening in the shoulder to view and or access soft tissue therein;
   forming a bone tunnel in the bone, wherein the bone tunnel comprises a slit extending to the upper edge of the humeral head;
   manipulating the torn rotator cuff tissue across the surface of the humeral head;
   suturing said tissue to obtain at least one free suture end;
   providing a bone anchor comprising a first component, said first component comprising an elongate shaft and a distal end, and a suture retaining channel at said distal end;
   engaging said suture in said channel;
   deploying said first component in the bone tunnel wherein deploying is performed after engaging, and wherein the suture is disposed within the slit along a suture path between the tissue and the first component; and
   locking said first component to prevent said suture from loosening wherein said locking is performed after said deploying step and wherein locking immobilizes said first component such that the first component is prevented from floating or otherwise moving in the bone tunnel.

2. The method of claim 1 wherein said locking step comprises manipulating a second component onto said first component of said anchor, wherein said second component is adapted to engage a proximal end of said first component of said anchor and said second component of said anchor comprises a lateral projection that lodges into a side wall of said bone tunnel thereby immobilizing the anchor and suture.

3. The method of claim 1 wherein said suturing step is performed with a preloaded suturing instrument.

4. The method of claim 3 wherein said suturing step is performed to provide a type of stitch selected from the group consisting of a mattress stitch and a Mason Allen stitch.

5. The method of claim 1 further comprising a tensioning step and wherein said tensioning comprises rotating said shaft of the bone anchor thereby wrapping the suture about said shaft.

6. The method of claim 1 wherein said surgery is performed arthroscopically.

7. The method of claim 2 wherein said second component comprises an anti-rotation cap.

8. A method for performing shoulder surgery to attach rotator cuff tissue to a target position adjacent a bone, said method comprising:
   providing a first anchor component having an elongate shaft, a distal end, and a suture retaining opening at said distal end,
   providing a second anchor component that engages a proximal end of said first anchor component;
   creating an opening in the shoulder to view and or access soft tissue therein;
   placing a suture through said tissue to obtain at least one free suture end;
   forming a bone tunnel in the bone, wherein the bone tunnel comprises a slit extending to the upper edge of the humeral head and along a suture path between the tissue and the first anchor component;
   engaging said suture with said first anchor component comprising looping a length of suture around the suture retaining opening without forming a knot in the length ot7suture;
   inserting said first anchor component in the bone tunnel after said engaging step, wherein the suture is disposed within the slit; and
   locking said suture without directly contacting said cuff tissue with an-the first and second anchor components.

9. The method of claim 8 wherein said second component comprises a radially disposed flange portion, and wherein the locking step comprises sliding the second component axially over the first component so as to lodge the flange portion into surrounding bone tissue.

10. The method of claim 8 wherein said placing step is performed with a preloaded suturing instrument.

11. The method of claim 8 comprising a tensioning step to move said tissue wherein said tensioning comprises rotating said shaft of the first component thereby wrapping the suture about said shaft.

12. The method of claim 8 wherein the locking step comprises sliding said second component axially and distally over the proximal end of the first component.

13. A method for performing shoulder surgery to attach rotator cuff tissue to an adjacent bone, said method comprising:
   creating an opening in the shoulder to view and or access soft tissue therein;
   forming a bone tunnel in the bone, wherein the bone tunnel comprises a slit extending to the upper edge of the humeral head;
   suturing said tissue to obtain at least one free suture end;
   engaging said suture with a bone anchor first component;
   deploying said bone anchor first component in the bone tunnel wherein deploying is performed after suturing, and wherein said deploying step situates said bone anchor first component entirely within the bone such that no portion of said bone anchor first component stands proud of said bone, and wherein the suture is disposed within the slit along a suture path between the tissue and the first component; and locking said suture in place to affix said tissue in said final position without further inserting said bone anchor first component in said tunnel wherein said locking is carried out by manipulating a second component onto said first component proximal end.

14. The method of claim 13 wherein said second component is an anti-rotation cap.

15. The method of claim 13 wherein said suturing is performed with a preloaded suturing instrument.

16. The method of claim 13 comprising tensioning said suture to move said tissue and wherein said tensioning comprises rotating an elongate shaft of the bone anchor thereby wrapping the suture about said shaft.

17. The method of claim 13 wherein the engagement step comprises looping at least one suture free end around the first component without forming a knot in the suture.

* * * * *

UNITED STATES PATENT AND TRADEMARK OFFICE
CERTIFICATE OF CORRECTION

| | | |
|---|---|---|
| PATENT NO. | : 8,109,966 B2 | Page 1 of 1 |
| APPLICATION NO. | : 11/779194 | |
| DATED | : February 7, 2012 | |
| INVENTOR(S) | : Mark A. Ritchart et al. | |

It is certified that error appears in the above-identified patent and that said Letters Patent is hereby corrected as shown below:

Column 16, line 36, "ot7 suture" should read --of suture--; line 41, "an-the" should be changed to --the--

Signed and Sealed this
Tenth Day of July, 2012

David J. Kappos
*Director of the United States Patent and Trademark Office*